United States Patent
Mashimo et al.

(10) Patent No.: US 10,362,771 B2
(45) Date of Patent: Jul. 30, 2019

(54) METHOD FOR KNOCK-IN OF DNA INTO TARGET REGION OF MAMMALIAN GENOME, AND CELL

(71) Applicant: KYOTO UNIVERSITY, Kyoto-shi, Kyoto (JP)

(72) Inventors: Tomoji Mashimo, Kyoto (JP); Kazuto Yoshimi, Kyoto (JP); Takehito Kaneko, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/528,506

(22) PCT Filed: Nov. 17, 2015

(86) PCT No.: PCT/JP2015/082279
§ 371 (c)(1),
(2) Date: May 20, 2017

(87) PCT Pub. No.: WO2016/080399
PCT Pub. Date: May 26, 2016

(65) Prior Publication Data
US 2017/0251647 A1 Sep. 7, 2017

(30) Foreign Application Priority Data

Nov. 20, 2014 (JP) .................................. 2014-235898

(51) Int. Cl.
| | | |
|---|---|---|
| C12N 15/63 | (2006.01) | |
| C12N 15/00 | (2006.01) | |
| C07H 21/04 | (2006.01) | |
| C07K 14/00 | (2006.01) | |
| A01K 67/027 | (2006.01) | |
| C12N 5/10 | (2006.01) | |
| C12N 15/09 | (2006.01) | |
| C12N 15/90 | (2006.01) | |
| C07K 14/315 | (2006.01) | |

(52) U.S. Cl.
CPC ........ *A01K 67/0278* (2013.01); *A01K 67/027* (2013.01); *C12N 5/10* (2013.01); *C12N 15/09* (2013.01); *C12N 15/907* (2013.01); *A01K 2207/15* (2013.01); *A01K 2217/052* (2013.01); *A01K 2217/072* (2013.01); *A01K 2227/105* (2013.01); *C07H 21/04* (2013.01); *C07K 14/315* (2013.01); *C12N 2800/10* (2013.01)

(58) Field of Classification Search
CPC .. C12N 15/907; C12N 2800/10; C07H 21/04; C07K 14/315
USPC .................. 435/320.1, 455; 536/23.1, 24.33; 530/350
See application file for complete search history.

(56) References Cited

FOREIGN PATENT DOCUMENTS

| | | |
|---|---|---|
| JP | 2004-180679 A | 7/2004 |
| WO | WO 2008/156668 A1 | 12/2008 |
| WO | 2011/158009 A1 | 12/2011 |
| WO | WO 2014/093635 A9 | 6/2014 |
| WO | WO 2014/172470 A2 | 10/2014 |

OTHER PUBLICATIONS

Dollé et al., "Evaluation of a plasmid-based transgenic mouse model for detecting in vivo mutations," *Mutagenesis,*, 11(1): 111-118 (1996).
Dicarlo et al., "Genome engineering in *Saccharomyces cerevisiae* using CRISPR-Cas systems," *Nucleic Acids Res.*, 41(7): 4336-4343 (2013).
Kuijpers et al., "One-step assembly and targeted integration of multigene constructs assisted by the I-SceI meganuclease in *Saccharomyces cerevisiae*," *FEMS Yeast Res.*, 13(8): 769-781 (2013).
European Patent Office, Extended European Search Report in European Patent Application No. 15861997.3 (dated Apr. 26, 2018).
Cui et al., *Nature Biotechnology*, 29(1): 64-67 (2011).
Dong et al., *The International Journal of Biochemistry and Cell Biology*, 55: 329-334 (2014).
Hsu et al., *Cell*, 157(6): 1262-1278 (2014).
Kimura et al., *Scientific Reports*, 4: 6545 (2014).
Mashimo, *Development, Growth & Differentiation*, 56(1): 46-52 (2014).
Olsen et al., *DNA Repair*, 8(3): 298-308 (2009).
Platt et al., *Cell*, 159(2): 440-455 (2014).
Ponce De León et al., *PLoS One*, 9(2): e88146 (2014).
Radecke et al., *Molecular Therapy*, 18(4): 743-753 (2010).
Seruggia et al., *Transgenic Research*, 23(5): 707-716 (2014).
Wang et al., *Cell*, 153(4): 910-918 (2013).
Yamamoto et al., "Genome Editing Technology Based on Site-specific Nucleases," *Virus*, 64(1): 75-82 (2014), English translation and Int'l Search Report.

(Continued)

*Primary Examiner* — Shin Lin Chen
(74) *Attorney, Agent, or Firm* — Leydig, Voit & Mayer, Ltd.

(57) ABSTRACT

This invention provides a method for knock-in of a donor DNA into the genome of a cell, comprising introducing at least one artificial nuclease system capable of cleaving target sequence(s) of the cell genome, the donor DNA, and two single-stranded oligonucleotides (ssODNs) into the cell, the artificial nuclease system cleaving the target sequence(s) on the cell genome, the two ssODNs each complementary to one of the ends generated by the target sequence cleavage in the cell genome and to one of the introduction ends of the donor DNA, the donor DNA being knocked-in at the cleavage site via the two ssODNs.

7 Claims, 16 Drawing Sheets
(16 of 16 Drawing Sheet(s) Filed in Color)
Specification includes a Sequence Listing.

(56) References Cited

OTHER PUBLICATIONS

Yang et al., *Cell*, 154(6): 1370-1379 (2013).
Yoshimi et al., "New Common sense of genome editing method CRISPR/Cas accelerates life science," *Experimental Medicine*, 32(11): 1715-1720 (2014), English translation and Int'l Search Report.
Yoshimi et al., *Nature Communications*, 5: 4240 (2014).
Yoshimi et al., *Nature Communications*, 7: 10431 (2016).
Japanese Patent Office, International Search Report in International Patent Application No. PCT/JP2015/082279 (dated Feb. 16, 2016), English translation.

Fig. 3
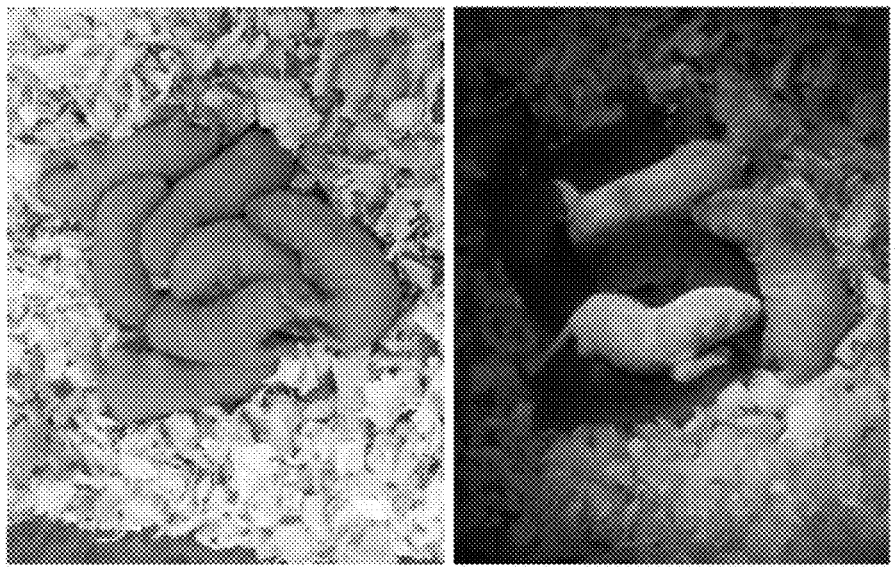
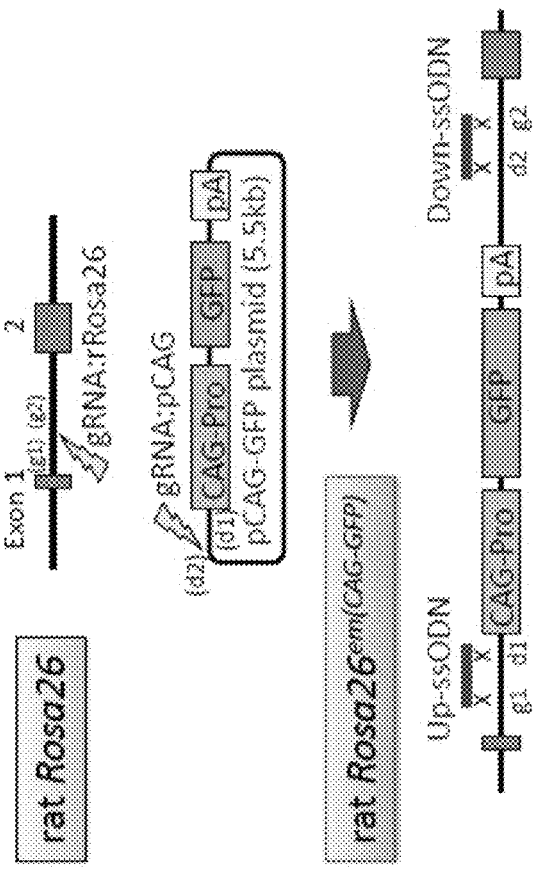

Fig.6

Rat Rosa26 locus SEQ ID NO: 87

Exon 1
▓▓▓▓▓▓▓▓▓▓▓▓▓▓▓▓▓▓▓▓▓▓GTAGGGGATCGGGACTCTGGCGGGAGGGTGGCTTGGCGCGTTTGCG
GGGGCGGCGGCCGCGGTAGGCCCTCCAAGGACGGTGGAGCCGCTTTGTGGGACAGCTGGGTTC
GATTCGTAACCCTGGAAGGGGCAAGCGGGTGGTAGTCAGGAATCCGGCCGCCCTGCAGCAACC
GGAGGGGGAGGGAGAAGGGAGCGGAAAAGTCTCCACCGGACGCGGCCATGGCTCCCACGGGGGG
CGGAGAAGCGCTTCCGGTCGATGTCTCATCGCTGATGGCTGCTTTCCTCCCGCCGCGTGTGA
AAACACAAATGGCGTGTTTTGGTTGGAGTGAGGCGCCTGTCAATTAACGGCTGCCGGAGTGCGC
AGCCGCTGACTGCCTCGCTGTGCCCACTGGGTGGGGCGGGAGGTAGGTGGGGTGAGGCGAGCTG
GACGTGCGGGCGCGGTCGGCCTCTGGCGGGGCGGGGGAGGGGAGGGTCAGCGAAAGTGGCTGGC
GCGTGAGCGGCCTCCCACCCTCCCCTTCCTCTGGGGAGTCGTTTTACCCGCCGCCGGCCTGGC <u>rRosa26 Large F</u>
CTCGTCATCTG[ATTGCTCTCGGGCTCAGAAACT]GGCCTTTGCAATTGGCCCGCGTTCATGC
AAGTTCAGTCCCTAAGCTGGCTGGCGGGGCGGCAGGGAGGCGCTCACAGGTTCCGGCCCTCCC
CCCAGGCCCCGCGCCGCAGAGTCTGGCCCCGCGCCCCTGCGCAACGTGGCAGGAAGCGCGCGCT
GGGGGCGGGGACGGGCGGTCGGTCTGAGCGGCGGGCGGGTGCAAACGGGATTCCTCCTTGAGTT
GTGGCACTGAGGAACGTGCTGAACAAGACCTACATTGCACTCCAGGGAGTGGATGAAGGAGTTG
GGGCTCAGTCGGGTTGTATTGGAGACAAGAAGCACTTGCTCTCCAAAAGTCGGTTTGAGTTATC <u>rRosa26 Small F</u>
ATT[AAGCAGCTGCAGTGGACTA]GGCGGAGAAAAGGCCGCACCCTTCTCAGGACGGGGGAGGGG
AGTGTTGCAATACCTTTCTGGAGTTCTCTGCTGCCTCCTGTCTTCTGAGGACCGCCCTGGGCC PAM rRosa26 target
TGGAAGATTCCCTTCCCCCTTCTTCC▼GGATCTCAACCAGAGCCTTTCTGGAAGATAGGC
GGGAGTCTTCTGGGCAGGCTTAAAGGCTAACCTGGTGCGTGGGCGTTGTCCTGCAGAGGAATT
GAACAGGTGTAAAATTGGAGGGGCAAGACTTCCCACAGATTTTCGATTGTGTTGTTAAGTATTG <u>rRosa26 Small R</u>
TAATAGGGGCAAATAAGGGAAAT[AGACTAGGCACTCACCTGG]GTTTTATGCAGCAAAACTACA
GGTTATTATTGCTTGTGATCCGCCCTGGAGAATTTTCACCGAGGTAGATTGAAGACATGCCCA
CCCAAATTTTAATATTCTTCCACTTGCGATCCTTGCTACAGTATGAAATTACAGTATCGTGAAT
TAGAATATATAAGCAGAATTTTAAGCATTTAAAAGAGCCCAGTACTTCATGTCTGTCTCTCCC
ACTTCTGCAGCCCTATCAAAGGGTATTTTAGCACACTCATTTTAGTCCCATTTTCATTTGTTGT
ACTGGCTTATCCAATCCCTAGACAGA[GCACTGGCATTCCCTCTCTCCT]
                            <u>rRosa26 Large R</u>

Fig. 7 pCAG-GFP vector (5497bp) SEQ ID NO: 38 pCAGGS Large F
TCAAGGCGAGTTACATGATCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTC
TGAGAATAGTGTATGCGGCGACCGAGTTGCTCTTGCCCGGCGTCAATACGGGATAATACCGCGC
CACATAGCAGAACTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAACTGATCTTCAGCA pCAGGS Small F
TCTTTTACTTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATTGAAGCAT pCAGGS_target SNM
TTATCAGGGTTATTGTCTCATGAGCGGATACATATTTGAATGTATTTAGAAAAATAAACAAATA GGGGTTCCGCGCACATTTCCCCGAAAAGTGCCACCTGGGTCGACATTGATTATTGACTAGTTAT pCAGGS Small R
TAATAGTAATCAATTACGGGGTCATTAGTTCATAGCCCATATATGGAGTTCCGCGTTACATAAC
TTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGG
TAAACTGCCCACTTGGCAGTACATCAAGTGTATCATATGCCAAGTACGCCCCCTATTGACGTCA pCAGGS Large R
ATGACGGTAAATGGCCCGCCTGGCATTATGCCCAGTACATGACCTTATGGGACTTTCCTACTTG
GCAGTACATCTACGTATTAGTCATCGCTATTACCATGGTCGAGGTGAGCCCCACGTTCTGCTTC CAG promoter + 1200bp TTCTGGCGTGTGACCGGCGGGTCTAGAGCCTCTGCTAACCATGTTCATGCCTTCTTCTTTTTCC
TACAGCTCCTGGGCAACGTGCTGGTTATTGTGCTGTTAAC GFP protein (720bp)

AC
TCCTCAGGTGCAGGCTGCCTATCAGAAGGTGGTGGCTGGTGTGGCCAATGCCCTGGCTCACAAA
TACCACTGA beta-globin poly(A) + 400bp

Fig. 8

**CRISPR-mediated KO/KI mutations at rat *Rosa26* loci**

| Wistar | | CCAGAAAGACTCCAGTTGCAGATCACGAGGGAAGAAGGG | SEQ ID NO: 39 |
|---|---|---|---|
| #1-1 | -1 | CCAGAAAGACTCCAGTTGCAGATCG-GAGGGAAGAAGGG | SEQ ID NO: 110 |
| #1-2 | -2 | CCAGAAAGACTCCAGTTGCAGA--ACGAGGGAAGAAGGG | SEQ ID NO: 111 |
| #1-3 | -6 | CCAGAAAGACTCCAGTTGCA------GAGGGAAGAAGGG | SEQ ID NO: 112 |
| | +35 | AGACTCCAGTTGCAGATCATGAG (+25bp) TAATAACGAGGGAAG (SEQ ID NO: 113) (SEQ ID NO: 114) | |
| #1-5 | -2 | CCAGAAAGACTCCAGTTGCAGA--ACGAGGGAAGAAGGG | SEQ ID NO: 115 |
| #1-6 | KI-6 | AGACTCCAGTTGCAGATCATGAG (pCAG-GFP) CGG------GGGAAG (SEQ ID NO: 116) | |
| | +1 | CCAGAAAGACTCCAGTTGCAGATCGACGAGGGAAGAAGGG | SEQ ID NO: 40 |
| #1-7 | KI+27 -256 | GCAGATA (+24bp) GACTGAG (pCAG-GFP) CGCTG (Δ256bp) CCGCC | SEQ ID NO: 117 |
| #1-8 | -506 | TACAA------------(Δ506bp)------------CAGGC | SEQ ID NO: 118 |
| #1-9 | +1 | CCAGAAAGACTCCAGTTGCAGATCAACGAGGGAAGAAGGG | SEQ ID NO: 41 |
| | +42 | AGACTCCAGTTGCAGATCATGAG (+32bp) CAATGACGAGGAAG (SEQ ID NO: 119) (SEQ ID NO: 120) | |
| #1-10 | -106 | CCAGAAAGACTCC---(Δ106bp)-----------CCCCT | SEQ ID NO: 121 |
| #1-11 | KI | AGACTCCAGTTGCAGATCATGAG (pCAG-GFP) CGCTGACGAGGAAG (SEQ ID NO: 122) (SEQ ID NO: 123) | |
| | +54 | AGACTCCAGTTGCAGATCATGAG (+44bp) TCCGACGAGGGAAG (SEQ ID NO: 124) (SEQ ID NO: 125) | |
| #1-12 | +11 | AGACTCCAGTTGCAGATCATGAGACAATAACGAGGGAAG | SEQ ID NO: 42 |
| | +43 | AGACTCCAGTTGCAGATCATGAG (+33bp) AAATAACGAGGGAAG (SEQ ID NO: 126) (SEQ ID NO: 127) | |
| #1-14 | +4 | CCAGAAAGACTCCAGTTGCAGATCTGCTACTAGGAAG | SEQ ID NO: 43 |

Fig.10

Mouse Rosa26 locus SEQ ID NO: 44

Exon 1
▓▓▓▓▓▓▓▓▓▓▓▓▓▓▓▓▓▓▓▓▓▓GTAGGGGATCGGGACTCTGGCGGGAGGGCGGCTTGGTGCGTTTGCG
GGGATGGGCGGCCGCGGCAGGCCCTCCGAGCGTGGTGGAGCCGTTCTGTGAGACAGCCGGGTAC
GAGTCGTGACGCTGGAAGGGGCAAGCGGGTGGTGGGCAGGAATGCGGTCCGCCCTGCAGCAACC
GGAGGGGAGGGAGAAGGGAGCGGAAAAGTCTCCACCGGACGCGGCCATGGCTCGGGGGGCGG
GGGCAGCGGAGGAGCGCTTCCGGCCGACGTCTCGTCGCTGATTGGCTTCTTTTCCTCCCGCCGT
GTGTGAAAACACAAATGGCGTGTTTTGGTTGGCGTAAGGCGCCTGTCAGTTAACGGCAGCCGGA
GTGCGCAGCCGCCGGCAGCCTCGCTCTGCCCACTGGGTGGGGCGGGAGGTAGGTGGGGTGAGGC
GAGCTGGACGTGCGGGCGCGGTCGGCCTCTGGCGGGGCGGGGGAGGGGAGGGAGGGTCAGCGAA
AGTAGCTCGCGCGCGAGCGGCCGCCCACCCTCCCCTTCCTCTGGGGGAGTCGTTTTACCCGCCG mRosa26 Large F
CCGGCCGGGCCTCGTCGTCTG[ATTGGCTCTCGGGGCCCAGAAAACT]GGCCCTTGCCATTGGCTC
GTGTTCGTGCAAGTTGAGTCCATCCGCCGGCCAGCGGGGGCGGCGAGGAGGCGCTCCCAGGTTC
CGGCCCTCCCCTCGGCCCCGCGCCGCAGAGTCTGGCCGCGCGCCCCTGCGCAACGTGGCAGGAA
GCGCGCGCTGGGGGCGGGGACGGGCAGTAGGGCTGAGCGGCTGCGGGGCGGGTGCAAGCACGTT
TCCGACTTGAGTTGCCTCAAGAGGGGCGTGCTGAGCCAGACCTCCATCGCGCACTCCGGGGAGT
GGAGGGAAGGAGCGAGGGCTCAGTTGGGCTGTTTTGGAGGCAGGAAGCACTTGCTCTCCCAAAG mRosa26 Small F
TCGCTCTGAGTTGTTATCAGT[AAGGCAGCTGCAGTGGAGTA]GGCGGGGAGAAGGCCGCACCCTT
CTCCGGAGGGGGAGGGGAGTGTTGCAATACCTTTCTGGGAGTTCTCTGCTGCCTCCTGGCTTC
                                        PAM   mRosa26_target
TGAGGACC▓▓▓▓▓CTGGGCCTGGGAGAATCCCTTCCCCCTCTTCC▼▓▓▓▓▓▓▓▓▓▓▓▓▓▓▓▓▓▓
▓▓▓▓▓▓▓▓▓▓▓▓▓▓▓▓▓▓▓▓▓▓▓▓▓▓▓▓TTCTGGGCAGGCTTAAAGGCTAACCTGGTGTGTGGGCGTT mRosa26 Small R
GTCCTGCAGGGGAATTGAACAGGTGTAAAATTGGAGGGACAA[GACTTCCCACAGATTTTCGG]TT
TTGTCGGGAAGTTTTTTAATAGGGGCAAATAAGGAAAATGGGAGGATAGGTAGTCATCTGGGT
TTTATGCAGCAAAACTACAGGTTATTATTGCTTGTGATCCGCCTCGGAGTATTTTCCATCGAGG
TAGATTAAAGACATGCTCACCCGAGTTTTATACTCTCCTGCTTGAGATCCTTACTACAGTATGA
AATTACAGTGTCGCGAGTTAGACTATGTAAGCAGAATTTTAATCATTTTAAAGAGCCCAGTAC
TTCATATCCATTTCTCCCGCTCCTTCTGCAGCCTTATCAAAAGGTATTTTAGAACACTCATTTT
AGCCCCATTTTCATTTATTATACTGGCTTATCCAACCCCTAGACAGA[GCATTGGCATTTTCCCT
TTCCT]
                                                    mRosa26_Large R

Fig.12

**CRISPR-mediated KO/KI mutations at mouse *Rosa26* loci**

```
C57BL/6    TCAGAAAGACTGGAGTTGCAGATCACGAGGGAAGAGGGG    SEQ ID NO: 62

#1-1   KI  AGACTGGAGTTGCAGATCATGAG (pCAG-GFP) CTCTGACGAGGGAAG
               SEQ ID NO: 128              SEQ ID NO: 130

+1  TCAGAAGACTGGAGTTTCAGATCGACGAGGGAAGAGGGG    SEQ ID NO: 53

#1-2  +69  TCAGAAAGACTGGAGTTGCAGATCATGAG (+69bp) CTTCAACGAGGGAAGAGGGG
                       SEQ ID NO: 131                    SEQ ID NO: 132

#1-3   -6  TCAGAAAGACTGGAGTTGCA------GAGGGAAGAGGGG    SEQ ID NO: 133

#1-4   +1  TCAGAAAGACTGGAGTTTCAGATCGACGAGGGAAGAGGGG   SEQ ID NO: 54

#1-5  -18  TCAGAAAGACT-------------------GGAAGAGGGG   SEQ ID NO: 134

#1-6  -60  GTTAGAGG-------(-63bp)-------GGGAAGAGGGG   SEQ ID NO: 135
```

Fig. 13
a
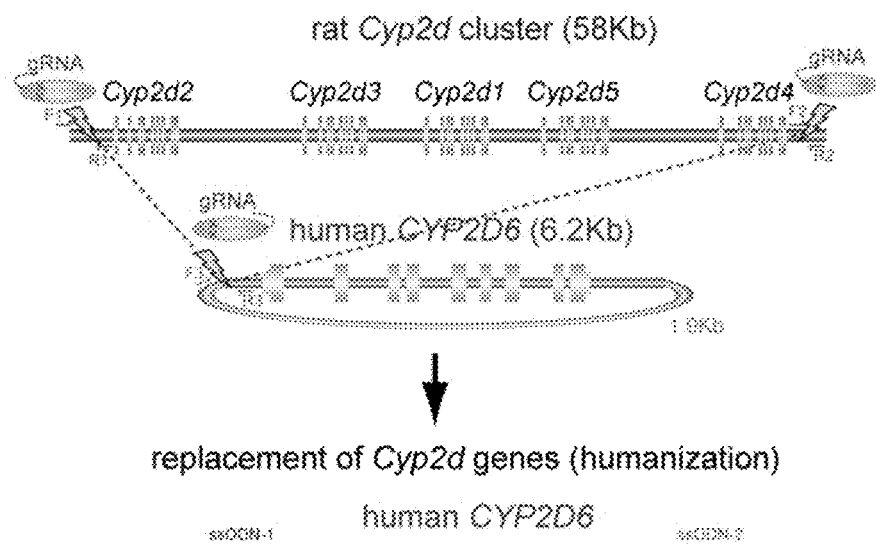
b
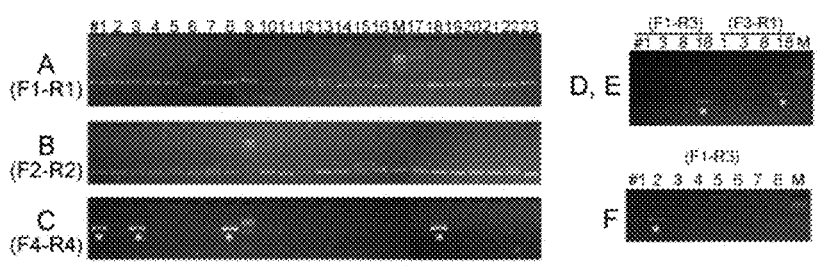
c
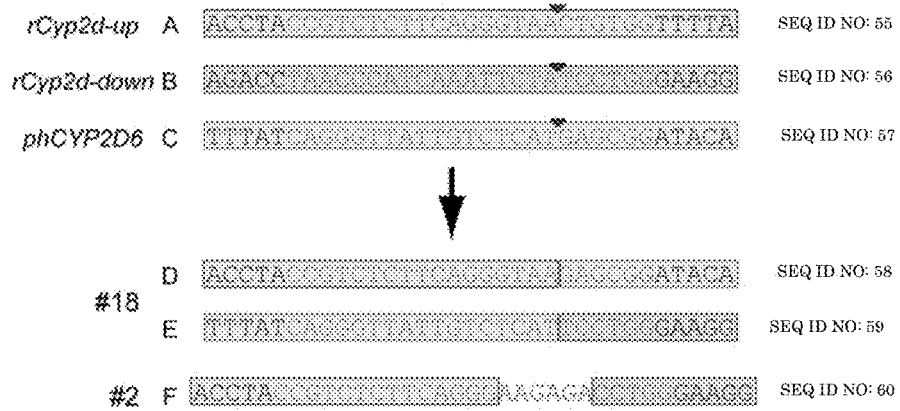

Fig.14

```
rCyp2d1-5 (58Kbp)    SEQ ID NO: 61
rCyp2d-up_Large_F
GACCTCCACACCTGTCTG GTACTTATCTCACAGGACTGAGCTGGCTAGGTTGTCCCCAGGCCTGCAAAGAGGC
TGGCGCCATCTGTTCTCAGGCTCTTGGGCATCCAGCCACCACTGGAAACTGAAAGAGCTGAGAACAGAGTGGA
GGCCGCAGGCTGGATCTAGCCGGAGGCTCAGTGGGAAAGCGGTGCTCCAGCTGGTCCTGCAGGGCGGGTCCTTG
GCTCAATGGAGCAGGTTTCACTTAGCCTGGTGCTGCCTGCCTCTGGGAGCAAAGTGAGGCCTTCTATGCCTTC
TCTGTGGCTTTCTGTGGCAGATCCCAATGAAAAGACACAGTCCATGATTTAAGGTATTTATTCTCATGGTAGAA
AGTGGATGAGTAGAACTGTACTGCACTTCTGAGCGTGGGCCTCAGATTAAGTACTTTTGCAGGAATGAGTGTTTG
GGAAGAAAGGTTATTGGCTCAGTCTCCAGGCTTTTAGGTACCTCATTATAATGGAGATCTGACTTGAAATGACCA
GGTCAGCTCCTCTCCATGTC GAGGGGCTTGGGGCATGCCCTTACATGACTGATGGCAACAAATGTATGGGGGC
rCyp2d-up_Small_F                                           rCyp2d-up_target PAM
TGCGGCTAGTGACAGGGCCTGGTGCCCAGGAGTCAGGCAAAACACCTAC                  CGTTGCTTTT
AAGGCTTAGCTCAACTGGGAATCAGGGTGCCTTTGACAGTCCCACAGGGATTGACCTATCAAGAAGACAAGGATG
AATGAAATTAGATAGTGGTCTCCATGAGA CAACCACCTGGACTCCTAGC TGGTCTCCCCAGGACTCTTGACAGTT
                              rCyp2d-up_Small_R
GGTGACAACCTTCAGCTTTGTCAGGTGACAGCTAAGAAGTCCCTAGGTTTTGAATTGGCCATCCTTGAGACTT
GAACGACCTTCCACCTGTACTTGAAGCTTCACAGGCTGGAGTTACCTTCCTCACACTGCCTCTCCCTCACCCTCA
TCAGCTACCCACACAAGCCACTTCAGTGGCCCTTGCTGCATACTGATAGTGGCCATGGTGTCAGTCAGACCCAT
GTCTGACTAGCCAAGTGTTTCTGGAAGCCTCCAAAAGTTCCTCTTCCAATCTGAGACGATGCCCTCAGGCCCGT
GGATCTCTGCCCATAAGGCAAATCAGCAGCTTGCACACTGAGGAAGGGTTCATGTTATGTGCTTGTCTTGCTCAA
AATGTCCAGCCCAACATAACCACTATGCTGCTTTCTGTGCAGATTTCAATGCCACTCCATGGACAAG ACCATC
                                                                rCyp2d-up_Large_R
GGAGATAACAAAC GGCAAGAACCTCTGATGTTTATTTTCCCTGGACTTTTCTGACACCCCTTCCTCCCATACAGGC
TCTGTTGAACATTAACACAGCTACTTGGCTCAATGTAGAGAACAAAGTGCAGCTTTACCCCCT
Cyp2d2_Exon_1
       rCyp2d1-6 55Kbp                                              Cyp2d4 Exon 9
                                                       AACGAATCATCCCTGT
CAGCCTCTCCAGCCTGTAAGGGGCCTCAGCAGCCTTCCCGTGGACATCCGCACCCCTACTTAATCTTCCTTGACCA
TGTGCCCCAATGGAAGGGCTGCTCTACTGACCTCCGAAATGGCAGCCATTCTTGCTTTCACCCCTGCCCCCTCTT
                                       rCyp2d-down_Large_F
TTCACCCAAATTGATGATGTCTATTCATAG ATGCCAACATCTGGAAGGAG GGCCAGAAAGGACTGCTGTGAAGGG
TCAGGTAAGTCACACAGATGAGGGAAGGGCGGTGGAGGTAATGGTGGGCAGAATTGTCCCCTTCCACTTGGAG
ATGTTTCTCCCAGACGCCCCATTTCAGACCCACTACACAACCAAGGCTAACTCCTCAGCCAGCATCATGACAAC
TTCTTATATGACGTCGCAGAGATGTAGAGAAGTCGGGGAGGCTGGAAATGACATGCAGGTTAAGTGCCCAAGGTT
ACCTGTTGGGTACCACATGCTTCCCTAAACGGTTTTGTGGGGGTCCAGAAGCAGGTTGCCTCCTAAGCTTCTTTG
TCACCATTAATTCCATGACCCAGCAGGGATACTGGTGTCCAGGCCCATGCACAGTAAGAAAGTGACTCTAACCAG
GGATGGAAGGACCCGCAAGCTTAGTGTTGACACAGACTCCCAGACCTTAGCACAACTGACTCCATGGTAGAAGTA
CCATTGGCCATAAAATT AGCACGTAGACAGCAGCTCCTCTCATAATGAAAACAAAGACCT
      rCyp2d-down_Small_F                                        rCyp2d-down_target
                    GAAGGTCTCTTGAAGCACTCCTCTTGGCTTCTTGGCTTCTGTAGTTCTCTAGC AACTGCTCTT
GCTAACTGAAGTATGTCAACCCAGGATATGGTTGTTGGTAAAAGCTCGCCCTGAGAACAGCTCAGGACGACATTG
AGGTGACC AGTGTAGTCACCAGCCAGC AATAAAGACCTCCTTTTGGTTTAAATCCATATCTGAGTAGTCTTCT
        rCyp2d-down_Small_R
CTGGTGCATACCTCACACCATTTCTAAAGGTTGCAACAAGATCCCTAGAGACAGACCTTGAGGCACCATGGGTCT
CAGATCCCATGGTGCAGAGAAGAGGAGTATGGTAGTCTAGGGGCTCCCAGGAAGTGTGCAACCAGAAGACTTTC
CAGGGCCTTAGGACTGCCTTTGATCATTTGCTGCCTAAAAGCTTTCTGACACTGCACCTCCCCCCCAAAAGAAA
CAAACTCAAGTGTTGCCTGGTCCGTTACCTCCAGAGGCTCTGTGTCCCTCTGTTAGGTAGGGCTGACCCAGTGTC
TGGGATCCAGGTGAGACATTACCAGACTCCCTGGCCTGTCTGTATGAATGTATGGTGACCACCCCTGCTTGTCT
TTACGTGTGCCTTTCTATATGATTCTGTCAGTTCTATAGACTGGAGAAACAT GAAAGTAGAAAGGGAACAGTT
                                                        rCyp2d-down_Large_R
```

Fig.15

**CRISPR-mediated indel mutations at rat *Cyp2d-up* and *Cyp2d-down* loci**

SEQUENCE LISTING

<160> NUMBER OF SEQ ID NOS: 172

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
tagggactcc agttgcagat cacg                                          24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
aaaccgtgat ctgcaactgg agtc                                          24

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
tagggactgg agttgcagat cacg                                          24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
aaaccgtgat ctgcaactcc agtc                                          24

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
taggcagggt tattgtctca tgag                                          24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
aaacctcatg agacaataac cctg                                          24

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
taggccgtct cttcagggta actg                                          24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
aaaccagtta ccctgaagag acgg                                              24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
taggtaaccc atcaaattct atcc                                              24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
aaacggatag aatttgatgg gtta                                              24

<210> SEQ ID NO 11
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 11
ccctgggcct ggaagattcc cttcccccctt cttccctcgt gagcggatac atatttgaat     60
gtatttagaa aaataaacaa                                                   80

<210> SEQ ID NO 12
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 12
ttcaatatta ttgaagcatt tatcagggtt attgtctcat gatctgcaac tggagtcttt     60
ctggaagata ggcgggagtc                                                   80

<210> SEQ ID NO 13
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 13
gccctgggcc tgggagaatc ccttccccct cttccctcgt gagcggatac atatttgaat     60
gtatttagaa aaataaacaa                                                   80

<210> SEQ ID NO 14
<211> LENGTH: 80
<212> TYPE: DNA
<213> ORGANISM: Artificial Sequence
<220> FEATURE:

<223> OTHER INFORMATION: Synthetic oligonucleotide

<400> SEQUENCE: 14
ttcaatatta ttgaagcatt tatcagggtt attgtctcat gatctgcaac tccagtcttt      60
ctagaagatg ggcgggagtc                                                  80

<210> SEQ ID NO 15
<211> LENGTH: 120
<212> TYPE: DNA
<213> ORGANISM: Artificial Sequence
<220> FEATURE:
<223> OTHER INFORMATION: Synthetic oligonucleotide

<400> SEQUENCE: 15
ctagtgacag ggcctggtgc ccaggagtca ggcaaaacac ctaccgtctc ttcagggtaa      60
gagcggatac atatttgaat gtatttagaa aaataaacaa atagggttc cgcgcacatt     120

<210> SEQ ID NO 16
<211> LENGTH: 120
<212> TYPE: DNA
<213> ORGANISM: Artificial Sequence
<220> FEATURE:
<223> OTHER INFORMATION: Synthetic oligonucleotide

<400> SEQUENCE: 16
aatactcata ctcttccttt ttcaatatta ttgaagcatt tatcagggtt attgtctcat      60
tcctgggaag gtctcttgaa gcactcatct tggcttcttg gcttctgtag ttctcctagc    120

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aagggagctg cagtggagta                                                  20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
cccaggtgag tgcctagtct                                                  20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
aagggagctg cagtggagta                                                  20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ccgaaaatct gtgggaagtc                                             20

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
ctaccccgac cacatgaag                                              19

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
cttgtgcccc aggatgtt                                               18

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
actttcacca gcgtttctgg                                             20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
aatcaatgtc gacccaggtg                                             20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ggtcacctcc tctccatgtg                                             20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gctaggagtc caggtgcttg                                             20

<210> SEQ ID NO 27

<211> LENGTH: 20
<212> TYPE: DNA
<213> ORGANISM: Artificial Sequence
<220> FEATURE:
<223> OTHER INFORMATION: primer

<400> SEQUENCE: 27
ccatttgggc cataaaactt                                               20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gctggctggt gactacactg                                               20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
tggcatgaag gactggattt                                               20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
aaggcctttc cttctggtgt                                               20

<210> SEQ ID NO 31
<211> LENGTH: 33
<212> TYPE: DNA
<213> ORGANISM: Rattus norvegicus

<400> SEQUENCE: 31
tcttccctcg tgatctgcaa ctggagtctt tct                                33

<210> SEQ ID NO 32
<211> LENGTH: 34
<212> TYPE: DNA
<213> ORGANISM: Rattus norvegicus

<400> SEQUENCE: 32
atttatcagg gttattgtct catgagcgga taca                               34

<210> SEQ ID NO 33
<211> LENGTH: 36
<212> TYPE: DNA
<213> ORGANISM: Rattus norvegicus

<400> SEQUENCE: 33
tcagggttat tgtctcatga tctgcaactg gagtct                             36

<210> SEQ ID NO 34
<211> LENGTH: 34

```
<212> TYPE: DNA
<213> ORGANISM: Rattus norvegicus

<400> SEQUENCE: 34
atttatcagg gttattgtct catgagcgga taca                               34

<210> SEQ ID NO 35
<211> LENGTH: 22
<212> TYPE: DNA
<213> ORGANISM: Rattus norvegicus

<400> SEQUENCE: 35
tcttccctcg tgagcggata ca                                           22

<210> SEQ ID NO 36
<211> LENGTH: 36
<212> TYPE: DNA
<213> ORGANISM: Rattus norvegicus

<400> SEQUENCE: 36
tcagggttat tgtctcatga tctgcaactg gagtct                            36

<210> SEQ ID NO 37
<211> LENGTH: 1648
<212> TYPE: DNA
<213> ORGANISM: Rattus norvegicus

<400> SEQUENCE: 37
tcagagagcc tcggctaggt aggggatcgg gactctggcg ggagggtggc ttggcgcgtt    60
tgcgggggcg ggcggccgcg gtaggccctc caaggacggt ggagccgctt tgtgggacag   120
ctgggttcga ttcgttaacc ctggaagggg caagcgggtg gtagtcagga atccggccgc   180
cctgcagcaa ccggaggggg agggagaagg gagcggaaaa gtctccaccg gacgcggcca   240
tggctcccac gggggcgga gaagcgcttc cggtcgatgt ctcatcgctg attggctgct    300
tttcctcccg ccgcgtgtga aaacacaaat ggcgtgtttt ggttggagtg aggcgcctgt   360
caattaacgg ctgccggagt gcgcagccgc tgactgcctc gctgtgccca ctgggtgggg   420
cgggaggtag gtggggtgag gcgagctgga cgtgcgggcg cggtcggcct ctggcggggc   480
gggggagggg agggtcagcg aaagtggctg gcgcgtgagc ggcctccac cctcccttc    540 ctctggggga gtcgttttac ccgccgccgg cctggcctcg tcatctgatt ggctctcggg   600
gctcagaaaa ctggcctttg caattggccc gcgttcatgc aagttcagtc cctaagctgg   660
ctggcggggg cggcagggag gcgctcacag gttccggccc tccccccagg ccccgcgccg   720
cagagtctgg ccccgcgccc ctgcgcaacg tggcaggaag cgcgcgctgg gggcggggac   780
gggcggtcgg tctgagcggc gggcgggtgc aaacgggatt cctccttgag ttgtggcact   840
gaggaacgtg ctgaacaaga cctacattgc actccaggga gtggatgaag gagttggggc   900
tcagtcgggt tgtattggag acaagaagca cttgctctcc aaaagtcggt ttgagttatc   960
attaagggag ctgcagtgga gtaggcggag aaaaggccgc acccttctca ggacggggga  1020
ggggagtgtt gcaatacctt tctgggagtt ctctgctgcc tcctgtcttc tgaggaccgc  1080
cctgggcctg gaagattccc ttcccccttc ttccctcgtg atctgcaact ggagtctttc  1140
tggaagatag gcgggagtct tctgggcagg cttaaaggct aacctggtgc gtgggcgtt   1200 gtcctgcaga ggaattgaac aggtgtaaaa ttggaggggc aagacttccc acagattttc   1260
gattgtgttg ttaagtattg taatagggc aaataaggga aatagactag gcactcacct    1320
```

| | |
|---|---|
| ggggttttat gcagcaaaac tacaggttat tattgcttgt gatccgccct ggagaatttt | 1380 |
| tcaccgaggt agattgaaga catgcccacc caaattttaa tattcttcca cttgcgatcc | 1440 |
| ttgctacagt atgaaattac agtatcgtga attagaatat ataagcagaa ttttaagcat | 1500 |
| tttaaaagag cccagtactt catgtctgtc tctcccactt ctgcagccct atcaagggt | 1560 |
| attttagcac actcatttta gtcccatttt catttgttgt actggcttat ccaatcccta | 1620 |
| gacagagcac tggcattccc tctctcct | 1648 |

```
<210> SEQ ID NO 38
<211> LENGTH: 3178
<212> TYPE: DNA
<213> ORGANISM: Artificial Sequence
<220> FEATURE:
<223> OTHER INFORMATION: Synthetic vector

<400> SEQUENCE: 38
```

| | |
|---|---|
| tcaaggcgag ttacatgatc ccccatgttg tgcaaaaaag cggttagctc cttcggtcct | 60 |
| ccgatcgttg tcagaagtaa gttggccgca gtgttatcac tcatggttat ggcagcactg | 120 |
| cataattctc ttactgtcat gccatccgta agatgctttt ctgtgactgg tgagtactca | 180 |
| accaagtcat tctgagaata gtgtatgcgg cgaccgagtt gctcttgccc ggcgtcaata | 240 |
| cgggataata ccgcgccaca tagcagaact ttaaaagtgc tcatcattgg aaaacgttct | 300 |
| tcggggcgaa aactctcaag gatcttaccg ctgttgagat ccagttcgat gtaacccact | 360 |
| cgtgcaccca actgatcttc agcatctttt actttcacca gcgtttctgg gtgagcaaaa | 420 |
| acaggaaggc aaaatgccgc aaaaaaggga ataagggcga cacggaaatg ttgaatactc | 480 |
| atactcttcc ttttcaata ttattgaagc atttatcagg gttattgtct catgagcgga | 540 |
| tacatatttg aatgtattta gaaaaataaa caaatagggg ttccgcgcac atttccccga | 600 |
| aaagtgccac ctgggtcgac attgattatt gactagttat taatagtaat caattacggg | 660 |
| gtcattagtt catagcccat atatggagtt ccgcgttaca taacttacgg taaatggccc | 720 |
| gcctggctga ccgcccaacg acccccgccc attgacgtca ataatgacgt atgttcccat | 780 |
| agtaacgcca atagggactt tccattgacg tcaatgggtg gagtatttac ggtaaactgc | 840 |
| ccacttggca gtacatcaag tgtatcatat gccaagtacg ccccctattg acgtcaatga | 900 |
| cggtaaatgg cccgcctggc attatgccca gtacatgacc ttatgggact ttcctacttg | 960 |
| gcagtacatc tacgtattag tcatcgctat taccatggtc gaggtgagcc ccacgttctg | 1020 |
| cttcactctc cccatctccc cccctcccc accccaatt ttgtatttat ttattttta | 1080 |
| attattttgt gcagcgatgg gggcggggg gggggggggg cgcgcgccag gcggggcggg | 1140 |
| gcggggcgag gggcggggcg gggcgaggcg gagaggtgcg gcggcagcca atcagagcgg | 1200 |
| cgcgctccga aagtttcctt ttatggcgag gcggcggcg cggcggccct ataaaagcg | 1260 |
| aagcgcgcgg cgggcgggag tcgctgcgcg ctgccttcgc cccgtgcccc gctccgccgc | 1320 |
| cgcctcgcgc cgcccgcccc ggctctgact gaccgcgtta ctcccacagg tgagcgggcg | 1380 |
| ggacggccct tctcctccgg gctgtaatta gcgcttggtt taatgacggc ttgtttcttt | 1440 |
| tctgtggctg cgtgaaagcc ttgaggggct ccggagggc cctttgtgcg ggggagcgg | 1500 |
| ctcgggggt gcgtgcgtgt gtgtgtgcgt ggggagcgcc gcgtgcggct ccgcgctgcc | 1560 |
| cggcggctgt gagcgctgcg ggcgcggcgc ggggctttgt gcgctccgca gtgtgcgcga | 1620 |
| ggggagcgcg gccgggggcg gtgccccgcg gtgcgggggg ggctgcgagg ggaacaaagg | 1680 |
| ctgcgtgcgg ggtgtgtgcg tgggggggtg agcaggggt gtgggcgcgt cggtcgggct | 1740 |

-continued

```
gcaacccccc ctgcaccccc ctccccgagt tgctgagcac ggcccggctt cgggtgcggg    1800
gctccgtacg gggcgtggcg cggggctcgc cgtgccgggc gggggggtggc ggcaggtggg    1860 ggtgccgggc ggggcggggc cgcctcgggc cggggagggc tcggggggagg ggcgcggcgg    1920 cccccggagc gccggcggct gtcgaggcgc ggcgagccgc agccattgcc ttttatggta    1980
atcgtgcgag agggcgcagg gacttccttt gtcccaaatc tgtgcggagc cgaaatctgg    2040
gaggcgccgc cgcaccccct ctagcggggcg cggggcgaag cggtgcggcg ccggcaggaa    2100
ggaaatgggc ggggagggcc ttcgtgcgtc gccgcgccgc cgtccccttc tccctctcca    2160
gcctcggggc tgtccgcggg gggacggctg ccttcggggg gacggggca gggcggggtt    2220 cggcttctgg cgtgtgaccg gcggctctag agcctctgct aaccatgttc atgccttctt    2280
ctttttccta cagctcctgg gcaacgtgct ggttattgtg ctgttaacat ggtgagcaag    2340
ggcgaggagc tgttcaccgg ggtggtgccc atcctggtcg agctggacgg cgacgtaaac    2400
ggccacaagt tcagcgtgtc cggcgagggc gagggcgatg ccacctacgg caagctgacc    2460
ctgaagttca tctgcaccac cggcaagctg cccgtgccct ggcccaccct cgtgaccacc    2520
ttcacctacg gcgtgcagtg cttcgcccgc taccccgacc acatgaagca gcacgacttc    2580
ttcaagtccg ccatgcccga aggctacgtc caggagcgca ccatcttctt caaggacgac    2640
ggcaactaca agacccgcgc cgaggtgaag ttcgagggcg acaccctggt gaaccgcatc    2700
gagctgaagg gcatcgactt caaggaggac ggcaacatcc tggggcacaa gctggagtac    2760
aactacaaca gccacaaggt ctatatcacc gccgacaagc agaagaacgg catcaaggtg    2820
aacttcaaga cccgccacaa catcgaggac ggcagcgtgc agctcgccga ccactaccag    2880
cagaacaccc ccatcggcga cggccccgtg ctgctgcccg acaaccacta cctgagcacc    2940
cagtccgccc tgagcaaaga ccccaacgag aagcgcgatc acatggtcct gctggagttc    3000
gtgaccgccg ccgggatcac tctcggcatg gacgagctgt acaagtaatg ataaactcct    3060
caggtgcagg ctgcctatca gaaggtggtg gctggtgtgg ccaatgccct ggctcacaaa    3120
taccactgag atcttttttcc ctctgccaaa aattatgggg acatcatgaa gccccttg    3178
```

<210> SEQ ID NO 39
<211> LENGTH: 39
<212> TYPE: DNA
<213> ORGANISM: Rattus norvegicus

<400> SEQUENCE: 39

```
ccagaaagac tccagttgca gatcacgagg gaagaaggg                             39
```

<210> SEQ ID NO 40
<211> LENGTH: 40
<212> TYPE: DNA
<213> ORGANISM: Rattus norvegicus

<400> SEQUENCE: 40

```
ccagaaagac tccagttgca gatcgacgag ggaagaaggg                            40
```

<210> SEQ ID NO 41
<211> LENGTH: 40
<212> TYPE: DNA
<213> ORGANISM: Rattus norvegicus

<400> SEQUENCE: 41

```
ccagaaagac tccagttgca gatcaacgag ggaagaaggg                            40
```

<210> SEQ ID NO 42
<211> LENGTH: 39
<212> TYPE: DNA
<213> ORGANISM: Rattus norvegicus

<400> SEQUENCE: 42
agactccagt tgcagatcat gagacaataa cgagggaag                    39

<210> SEQ ID NO 43
<211> LENGTH: 39
<212> TYPE: DNA
<213> ORGANISM: Rattus norvegicus

<400> SEQUENCE: 43
ccagaaaaga ctccagttgc agatctgcta ctagggaag                    39

<210> SEQ ID NO 44
<211> LENGTH: 1669
<212> TYPE: DNA
<213> ORGANISM: Mus musculus

<400> SEQUENCE: 44
tcagagagcc tcggctaggt aggggatcgg gactctggcg ggagggcggc ttggtgcgtt    60
tgcggggatg ggcggccgcg gcaggccctc cgagcgtggt ggagccgttc tgtgagacag   120
ccgggtacga gtcgtgacgc tggaaggggc aagcgggtgg tgggcaggaa tgcggtccgc   180
cctgcagcaa ccggaggggg agggagaagg gagcggaaaa gtctccaccg gacgcggcca   240
tggctcgggg ggggggggc agcggaggag cgcttccggc cgacgtctcg tcgctgattg   300
gcttcttttc ctcccgccgt gtgtgaaaac acaaatggcg tgttttggtt ggcgtaaggc   360
gcctgtcagt taacggcagc cggagtgcgc agccgccggc agcctcgctc tgcccactgg   420
gtggggcggg aggtaggtgg ggtgaggcga gctggacgtg cgggcgcggt cggcctctgg   480
cggggcgggg gaggggaggg agggtcagcg aaagtagctc gcgcgcgagc ggccgcccac   540 cctcccccttc ctctgggga gtcgtttttac ccgccgccgg ccgggcctcg tcgtctgatt   600
ggctctcggg gcccagaaaa ctggcccttg ccattggctc gtgttcgtgc aagttgagtc   660
catccgccgg ccagcggggg cggcgaggag gcgctcccag gttccggccc tcccctcggc   720
cccgcgccgc agagtctggc cgcgcgcccc tgcgcaacgt ggcaggaagc gcgcgctggg   780
ggcggggacg ggcagtaggg ctgagcggct gcggggcggg tgcaagcacg tttccgactt   840
gagttgcctc aagaggggcg tgctgagcca gacctccatc gcgcactccg gggagtggag   900
ggaaggagcg agggctcagt tgggctgttt tggaggcagg aagcacttgc tctcccaaag   960
tcgctctgag ttgttatcag taagggagct gcagtggagt aggcggggag aaggccgcac  1020
ccttctccgg aggggggagg ggagtgttgc aataccttttc tgggagttct ctgctgcctc  1080
ctggcttctg aggaccgccc tgggcctggg agaatccctt cccccctcttc cctcgtgatc  1140 tgcaactcca gtctttctag aagatgggcg ggagtcttct gggcaggctt aaaggctaac  1200
ctggtgtgtg ggcgttgtcc tgcagggaa ttgaacaggt gtaaaattgg agggacaaga  1260
cttcccacag atttttcggtt ttgtcggaa gttttttaat aggggcaaat aaggaaaatg  1320
ggaggatagg tagtcatctg gggttttatg cagcaaaact acaggttatt attgcttgtg  1380
atccgcctcg gagtattttc catcgaggta gattaaagac atgctcaccc gagttttata  1440
ctctcctgct tgagatcctt actacagtat gaaattacag tgtcgcgagt tagactatgt  1500
aagcagaatt ttaatcattt ttaaagagcc cagtacttca tatccatttc tcccgctcct  1560

```
tctgcagcct tatcaaaagg tattttagaa cactcatttt agccccattt tcatttatta      1620
tactggctta tccaacccct agacagagca ttggcatttt ccctttcct                 1669

<210> SEQ ID NO 45
<211> LENGTH: 33
<212> TYPE: DNA
<213> ORGANISM: Rattus norvegicus

<400> SEQUENCE: 45
tcttccctcg tgatctgcaa ctccagtctt tct                                    33

<210> SEQ ID NO 46
<211> LENGTH: 34
<212> TYPE: DNA
<213> ORGANISM: Rattus norvegicus

<400> SEQUENCE: 46
atttatcagg gttattgtct catgagcgga taca                                   34

<210> SEQ ID NO 47
<211> LENGTH: 22
<212> TYPE: DNA
<213> ORGANISM: Rattus norvegicus

<400> SEQUENCE: 47
tcttccctcg tgagcggata ca                                                22

<210> SEQ ID NO 48
<211> LENGTH: 36
<212> TYPE: DNA
<213> ORGANISM: Rattus norvegicus

<400> SEQUENCE: 48
tcagggttat tgtctcatga tctgcaactc cagtct                                 36

<210> SEQ ID NO 49
<211> LENGTH: 22
<212> TYPE: DNA
<213> ORGANISM: Rattus norvegicus

<400> SEQUENCE: 49
tcttccctcg tgagcggata ca                                                22

<210> SEQ ID NO 50
<211> LENGTH: 40
<212> TYPE: DNA
<213> ORGANISM: Rattus norvegicus

<400> SEQUENCE: 50
tcttccctct tccctcttca tattgttatg agcggataca                             40

<210> SEQ ID NO 51
<211> LENGTH: 36
<212> TYPE: DNA
<213> ORGANISM: Rattus norvegicus

<400> SEQUENCE: 51
tcagggttat tgtctcatga tctgcaactc cagtct                                 36

<210> SEQ ID NO 52
<211> LENGTH: 39
<212> TYPE: DNA
```

<213> ORGANISM: Mus musculus

<400> SEQUENCE: 52
tcagaaagac tggagttgca gatcacgagg gaagagggg                       39

<210> SEQ ID NO 53
<211> LENGTH: 40
<212> TYPE: DNA
<213> ORGANISM: Mus musculus

<400> SEQUENCE: 53
tcagaaagac tggagttgca gatcgacgag ggaagagggg                      40

<210> SEQ ID NO 54
<211> LENGTH: 40
<212> TYPE: DNA
<213> ORGANISM: Mus musculus

<400> SEQUENCE: 54
tcagaaagac tggagttgca gatcgacgag ggaagagggg                      40

<210> SEQ ID NO 55
<211> LENGTH: 33
<212> TYPE: DNA
<213> ORGANISM: Rattus norvegicus

<400> SEQUENCE: 55
acctaccgtc tcttcagggt aactgtggtt tta                             33

<210> SEQ ID NO 56
<211> LENGTH: 33
<212> TYPE: DNA
<213> ORGANISM: Rattus norvegicus

<400> SEQUENCE: 56
agacctaacc catcaaattc tatcctggga agg                             33

<210> SEQ ID NO 57
<211> LENGTH: 33
<212> TYPE: DNA
<213> ORGANISM: Rattus norvegicus

<400> SEQUENCE: 57
tttatcaggg ttattgtctc atgagcggat aca                             33

<210> SEQ ID NO 58
<211> LENGTH: 33
<212> TYPE: DNA
<213> ORGANISM: Rattus norvegicus

<400> SEQUENCE: 58
acctaccgtc tcttcagggt aagagcggat aca                             33

<210> SEQ ID NO 59
<211> LENGTH: 33
<212> TYPE: DNA
<213> ORGANISM: Rattus norvegicus

<400> SEQUENCE: 59
tttatcaggg ttattgtctc attcctggga agg                             33

<210> SEQ ID NO 60
<211> LENGTH: 35

```
<212> TYPE: DNA
<213> ORGANISM: Rattus norvegicus

<400> SEQUENCE: 60
acctaccgtc tcttcaggga agagacctgg gaagg                           35

<210> SEQ ID NO 61
<211> LENGTH: 3149
<212> TYPE: DNA
<213> ORGANISM: Rattus norvegicus

<400> SEQUENCE: 61
gacctcccac acctgtctgt gtacttatct cacaggactg agctggctag gttgtcccca    60
ggcctgcaaa gaggctgggg cccatctggt tctcaggctc ttgggcatcc aggcaccact   120
ggaaactgaa agagctgaga acagagtgga ggcccgcagg ctggatctag ccggaggctg   180
agtgggaaag gggtgctcca gctggtcctg caggggagt  ccttggctca atggtagcag   240
gtttcactta gctggtggt  ggctgcctct gggagcaaag tgaggccttc tatggccttc   300
tctgtggctt tctgtggcag atcccaatga aaagagacag tccatgattt taaggtattt   360
attctcatgg tagaaagtgg atgagtagaa ctgtactgca cttctgaggg tgggcctcag   420
attaagtact tttgcaggaa tgagtgtttg ggaagaaagg ttattggctc agtctccagg   480
cttttaggta cctcattata atggagatct gacttgaaat gaccaggtca cctcctctcc   540
atgtggaggg gcttggggca ttgcccttac atgactgatg gcaacaaatg tatgggggc    600
tgcggctagt gacagggcct ggtgcccagg agtcaggcaa acacctacc  gtctcttcag   660
ggtaactgtg gttttaaggc ttagctcaac tgggaatcag ggtgcctttg acagtcccac   720
agggattgac ctatcaagaa gacaaggatg aatgaaatta gatagtggtc tccatgagac   780
aagcacctgg actcctagct ggtctcccca ggactcttga cagttggtga caacctttca   840
gctttgtcag gtgagagcta agaagtccct aggttttgaa tttggccatc cttgagactt   900
gaacgacctt ccacctgtac ttgaagcttc acaggctgga gttaccttcc tcacactgcc   960
tctccctcac cctcatcagc tacccacaca agccacttca gtggcccttg ctgcatactg  1020
atagtggcca tggtgtcagt cagaccccat gtctgactag ccaagtgttt ctggaagcct  1080
ccaaaagttc ctcttccaat ctgagacgat gccctcaggc ccgtggatc  tctgcccata  1140
aggcaaatca gcagcttgca cactgaggaa gggttcatgt tatgtgcttg tcttgctcaa  1200
aatgtccagc ccaacataac cactatgctg cttctgtgg  agatttcaat gccactccca  1260
tggacaagca ccaccggaga gaagaaaggg caagaacctc tgatgtttat tttcccctgga 1320
cttttctgac acccttccc  ccatacaggc tctgtttgaa cattaacaca gctacttggc  1380
tcaatttaga gaacaaagtg cagctttacc cccttttaag ggaccaggtt cccagtctgt  1440
tgtaagagga tctttcctga ttctaagtgt ctggacaagt attccttcaa aagcctgcaa  1500
gccgtggggc agccatgggg ctgctgattg gagatgacct ctgggctgtg gtcatattca  1560
cagccatctt cttgcactat ggcgtctttg gtgctctgac caccccgcgc ccctaccagc  1620
tctgtgcttc accccgctaa ggggaggcac agcatctcac tcactgtgct tgctggggtc  1680
ctagtgtgca ataaatggtt ttactctgaa ccgaatcatc cctgtgagct ctccaggctg  1740
taaggggcct gagcagcctt cccgtggaca tccgcacccc tacttaatct tccttgacca  1800
tgtgccccaa tggaagggct gctctactga cctccgaaat ggcagccatt cttgctttca  1860
cccctgcccc ctcttttcac ccaaattgat gatgtttatt catagatgcc aacatctgga  1920
```

```
aggagggcca gaaaggactg ctgtgaaggg tcagtgtaag tcacacagat gagggaaggg    1980
gcggtggagg taatggtggg cagaattgtc cccttttccac ttgagatgtt tctcccagac   2040
gcccccattt cagacccact acacaaccaa ggctaactcc tcagccagca tcatcacaac    2100
ttcttatatg acgtcgcaga gatgtagaga agtcggggag gctggaaatg acatgcaggt    2160
taagtgccca aggttacctg ttgggtacca catgcttccc taaacggttt tgtgggggtc    2220
cagaagcagg ttgcctccta agcttctttg tcaccattaa ttccatgacc cagcagggat    2280
actggtgtcc aggcccatgc acagtaagaa agtgactcta accagggatg aaggacccg     2340 caagcttagt gttgacacag actcccagac cttagcacaa ctgactccat ggtagaagta    2400
ccatttgggc cataaaactt agcacgtaga cagcagctcc tctcataatg aaaacaaaga    2460
cctaacccat caaattctat cctgggaagg tctcttgaag cactcctctt ggcttcttgg    2520
cttctgtagt tctcctagct aactgctctt gctaactgaa gtatgtcaac ccaggatatg    2580
gttgttggta aaagctcgcc ctgagaacag ctcaggacga cattgaggtg acccagtgta    2640
gtcaccagcc agctaataaa gacctccttt tggtttaaat ccatatctga gtagtcttct    2700
ctggtgcata cctcacacca tttctaaagg ttgcaacaag atccctagag acagaccttg    2760
aggcaccatg ggtctcagat ccccatggtg cagagaagag gagtatggta gtctaggggc    2820
tcccaggaag tgtgcaacca gaagactttc cagggcctta ggactgcctt tgatcatttg    2880
ctgcctaaaa gctttctgac actgcacctc cccccccaaa agaaacaaac tcaagtgttg    2940
cctggtccgt tacctccaga ggctctgtgt ccctctgtta ggtagggctg acccagtgtc    3000
tgggatccag gtgagacatt accagactcc cctggcctgt ctgtatgaat gtatggtgac    3060 caccccctgct tgtctttacg tgtgcctttc tatatgattc tgtcagttct atagactgga   3120
gaaacatcga aagtagaaag ggaacagtc                                      3149

<210> SEQ ID NO 62
<211> LENGTH: 33
<212> TYPE: DNA
<213> ORGANISM: Rattus norvegicus

<400> SEQUENCE: 62
acctaccgtc tcttcagggt aactgtggtt tta                                  33

<210> SEQ ID NO 63
<211> LENGTH: 34
<212> TYPE: DNA
<213> ORGANISM: Rattus norvegicus

<400> SEQUENCE: 63
acctaccgtc tcttcagggt aaactgtggt ttta                                 34

<210> SEQ ID NO 64
<211> LENGTH: 34
<212> TYPE: DNA
<213> ORGANISM: Rattus norvegicus

<400> SEQUENCE: 64
acctaccgtc tcttcagggt aaactgtggt ttta                                 34

<210> SEQ ID NO 65
<211> LENGTH: 36
<212> TYPE: DNA
<213> ORGANISM: Rattus norvegicus

<400> SEQUENCE: 65
```

```
acctaccgtc tcttcagggt agtttctgtg gtttta                                36
```

<210> SEQ ID NO 66
<211> LENGTH: 36
<212> TYPE: DNA
<213> ORGANISM: Rattus norvegicus

<400> SEQUENCE: 66

```
acctaccgtc tcttcagggt agtttctgtg gtttta                                36
```

<210> SEQ ID NO 67
<211> LENGTH: 33
<212> TYPE: DNA
<213> ORGANISM: Rattus norvegicus

<400> SEQUENCE: 67

```
acctaccgtc tcttcagggt aactgtggtt tta                                   33
```

<210> SEQ ID NO 68
<211> LENGTH: 33
<212> TYPE: DNA
<213> ORGANISM: Rattus norvegicus

<400> SEQUENCE: 68

```
agacctaacc catcaaattc tatcctggga agg                                   33
```

<210> SEQ ID NO 69
<211> LENGTH: 34
<212> TYPE: DNA
<213> ORGANISM: Rattus norvegicus

<400> SEQUENCE: 69

```
agacctaacc catcaaattc tattcctggg aagg                                  34
```

<210> SEQ ID NO 70
<211> LENGTH: 34
<212> TYPE: DNA
<213> ORGANISM: Rattus norvegicus

<400> SEQUENCE: 70

```
agacctaacc catcaaattc tactcctggg aagg                                  34
```

<210> SEQ ID NO 71
<211> LENGTH: 37
<212> TYPE: DNA
<213> ORGANISM: Rattus norvegicus

<400> SEQUENCE: 71

```
agacctaacc catcaaattc tattttcct gggaagg                                37
```

<210> SEQ ID NO 72
<211> LENGTH: 34
<212> TYPE: DNA
<213> ORGANISM: Rattus norvegicus

<400> SEQUENCE: 72

```
agacctaacc catcaaattc tattcctggg aagg                                  34
```

<210> SEQ ID NO 73
<211> LENGTH: 34
<212> TYPE: DNA
<213> ORGANISM: Rattus norvegicus

```
<400> SEQUENCE: 73
agacctaacc catcaaattc taatcctggg aagg                                    34

<210> SEQ ID NO 74
<211> LENGTH: 34
<212> TYPE: DNA
<213> ORGANISM: Rattus norvegicus

<400> SEQUENCE: 74
agacctaacc catcaaattc tactcctggg aagg                                    34

<210> SEQ ID NO 75
<211> LENGTH: 34
<212> TYPE: DNA
<213> ORGANISM: Rattus norvegicus

<400> SEQUENCE: 75
agacctaacc catcaaattc tactcctggg aagg                                    34

<210> SEQ ID NO 76
<211> LENGTH: 34
<212> TYPE: DNA
<213> ORGANISM: Rattus norvegicus

<400> SEQUENCE: 76
agacctaacc catcaaattc tactcctggg aagg                                    34

<210> SEQ ID NO 77
<211> LENGTH: 34
<212> TYPE: DNA
<213> ORGANISM: Rattus norvegicus

<400> SEQUENCE: 77
agacctaacc catcaaattc tacccctggg aagg                                    34

<210> SEQ ID NO 78
<211> LENGTH: 34
<212> TYPE: DNA
<213> ORGANISM: Rattus norvegicus

<400> SEQUENCE: 78
agacctaacc catcaaattc tactcctggg aagg                                    34

<210> SEQ ID NO 79
<211> LENGTH: 35
<212> TYPE: DNA
<213> ORGANISM: Rattus norvegicus

<400> SEQUENCE: 79
agacctaacc catcaaattc tatttcctgg gaagg                                   35

<210> SEQ ID NO 80
<211> LENGTH: 34
<212> TYPE: DNA
<213> ORGANISM: Rattus norvegicus

<400> SEQUENCE: 80
agacctaacc catcaaattc tactcctggg aagg                                    34

<210> SEQ ID NO 81
<211> LENGTH: 35
<212> TYPE: DNA
<213> ORGANISM: Rattus norvegicus
```

```
<400> SEQUENCE: 81
agacctaacc catcaaattc tatttcctgg gaagg                                35

<210> SEQ ID NO 82
<211> LENGTH: 33
<212> TYPE: DNA
<213> ORGANISM: Rattus norvegicus

<400> SEQUENCE: 82
agacctaacc catcaaattc tatcctggga agg                                  33

<210> SEQ ID NO 83
<211> LENGTH: 34
<212> TYPE: DNA
<213> ORGANISM: Rattus norvegicus

<400> SEQUENCE: 83
agacctaacc catcaaattc tattcctggg aagg                                 34

<210> SEQ ID NO 84
<211> LENGTH: 33
<212> TYPE: DNA
<213> ORGANISM: Rattus norvegicus

<400> SEQUENCE: 84
agacctaacc catcaaattc tatcctggga agg                                  33

<210> SEQ ID NO 85
<211> LENGTH: 34
<212> TYPE: DNA
<213> ORGANISM: Rattus norvegicus

<400> SEQUENCE: 85
agacctaacc catcaaattc tactcctggg aagg                                 34

<210> SEQ ID NO 86
<211> LENGTH: 37
<212> TYPE: DNA
<213> ORGANISM: Rattus norvegicus

<400> SEQUENCE: 86
agacctaacc catcaaattc tattttttcct gggaagg                             37

<210> SEQ ID NO 87
<211> LENGTH: 34
<212> TYPE: DNA
<213> ORGANISM: Rattus norvegicus

<400> SEQUENCE: 87
agacctaacc catcaaattc tattcctggg aagg                                 34

<210> SEQ ID NO 88
<211> LENGTH: 29
<212> TYPE: DNA
<213> ORGANISM: Rattus norvegicus

<400> SEQUENCE: 88
ttccctcgtg atctgcaact ggagtcttt                                       29

<210> SEQ ID NO 89
<211> LENGTH: 29
<212> TYPE: DNA
```

<213> ORGANISM: Rattus norvegicus

<400> SEQUENCE: 89
tatcagggtt attgtctcat gagcggata                    29

<210> SEQ ID NO 90
<211> LENGTH: 12
<212> TYPE: DNA
<213> ORGANISM: Rattus norvegicus

<400> SEQUENCE: 90
ttcccgcgga ta                                      12

<210> SEQ ID NO 91
<211> LENGTH: 40
<212> TYPE: DNA
<213> ORGANISM: Rattus norvegicus

<400> SEQUENCE: 91
tatcagggtt attgtctcat gatctgcaac tggagtcttt        40

<210> SEQ ID NO 92
<211> LENGTH: 14
<212> TYPE: DNA
<213> ORGANISM: Rattus norvegicus

<400> SEQUENCE: 92
ggcgggagcg gata                                    14

<210> SEQ ID NO 93
<211> LENGTH: 17
<212> TYPE: DNA
<213> ORGANISM: Rattus norvegicus

<400> SEQUENCE: 93
gggttattgt ctcagtc                                 17

<210> SEQ ID NO 94
<211> LENGTH: 12
<212> TYPE: DNA
<213> ORGANISM: Rattus norvegicus

<400> SEQUENCE: 94
tactctgcaa ct                                      12

<210> SEQ ID NO 95
<211> LENGTH: 14
<212> TYPE: DNA
<213> ORGANISM: Rattus norvegicus

<400> SEQUENCE: 95
gcctggagcg gata                                    14

<210> SEQ ID NO 96
<211> LENGTH: 29
<212> TYPE: DNA
<213> ORGANISM: Rattus norvegicus

<400> SEQUENCE: 96
tatcagggtt attgtctcat gagcggata                    29

<210> SEQ ID NO 97
<211> LENGTH: 18

```
<212> TYPE: DNA
<213> ORGANISM: Rattus norvegicus

<400> SEQUENCE: 97
ttccctcgtg agcggata                                              18

<210> SEQ ID NO 98
<211> LENGTH: 40
<212> TYPE: DNA
<213> ORGANISM: Rattus norvegicus

<400> SEQUENCE: 98
tatcagggtt attgtctcat gatctgcaac tggagtcttt                      40

<210> SEQ ID NO 99
<211> LENGTH: 33
<212> TYPE: DNA
<213> ORGANISM: Rattus norvegicus

<400> SEQUENCE: 99
tcttccctcg tgatctgcaa ctggagtctt tct                             33

<210> SEQ ID NO 100
<211> LENGTH: 34
<212> TYPE: DNA
<213> ORGANISM: Rattus norvegicus

<400> SEQUENCE: 100
atttatcagg gttattgtct catgagcgga taca                            34

<210> SEQ ID NO 101
<211> LENGTH: 16
<212> TYPE: DNA
<213> ORGANISM: Rattus norvegicus

<400> SEQUENCE: 101
tcttcccgcg gataca                                                16

<210> SEQ ID NO 102
<211> LENGTH: 36
<212> TYPE: DNA
<213> ORGANISM: Rattus norvegicus

<400> SEQUENCE: 102
tcagggttat tgtctcatga tctgcaactg gagtct                          36

<210> SEQ ID NO 103
<211> LENGTH: 16
<212> TYPE: DNA
<213> ORGANISM: Rattus norvegicus

<400> SEQUENCE: 103
ggcgggagcg gataca                                                16

<210> SEQ ID NO 104
<211> LENGTH: 14
<212> TYPE: DNA
<213> ORGANISM: Rattus norvegicus

<400> SEQUENCE: 104
ttattgtctc agtc                                                  14

<210> SEQ ID NO 105
```

```
<211> LENGTH: 12
<212> TYPE: DNA
<213> ORGANISM: Rattus norvegicus

<400> SEQUENCE: 105
tactctgcaa ct                                                        12

<210> SEQ ID NO 106
<211> LENGTH: 10
<212> TYPE: DNA
<213> ORGANISM: Rattus norvegicus

<400> SEQUENCE: 106
gcctgttgta                                                           10

<210> SEQ ID NO 107
<211> LENGTH: 34
<212> TYPE: DNA
<213> ORGANISM: Rattus norvegicus

<400> SEQUENCE: 107
atttatcagg gttattgtct catgagcgga taca                                34

<210> SEQ ID NO 108
<211> LENGTH: 22
<212> TYPE: DNA
<213> ORGANISM: Rattus norvegicus

<400> SEQUENCE: 108
tcttccctcg tgagcggata ca                                             22

<210> SEQ ID NO 109
<211> LENGTH: 36
<212> TYPE: DNA
<213> ORGANISM: Rattus norvegicus

<400> SEQUENCE: 109
tcagggttat tgtctcatga tctgcaactg gagtct                              36

<210> SEQ ID NO 110
<211> LENGTH: 38
<212> TYPE: DNA
<213> ORGANISM: Rattus norvegicus

<400> SEQUENCE: 110
ccagaaagac tccagttgca gatcggaggg aagaaggg                            38

<210> SEQ ID NO 111
<211> LENGTH: 37
<212> TYPE: DNA
<213> ORGANISM: Rattus norvegicus

<400> SEQUENCE: 111
ccagaaagac tccagttgca gaacgaggga agaaggg                             37

<210> SEQ ID NO 112
<211> LENGTH: 33
<212> TYPE: DNA
<213> ORGANISM: Rattus norvegicus

<400> SEQUENCE: 112
ccagaaagac tccagttgca gagggaagaa ggg                                 33
```

```
<210> SEQ ID NO 113
<211> LENGTH: 23
<212> TYPE: DNA
<213> ORGANISM: Rattus norvegicus

<400> SEQUENCE: 113
agactccagt tgcagatcat gag                                              23

<210> SEQ ID NO 114
<211> LENGTH: 15
<212> TYPE: DNA
<213> ORGANISM: Rattus norvegicus

<400> SEQUENCE: 114
taataacgag ggaag                                                       15

<210> SEQ ID NO 115
<211> LENGTH: 37
<212> TYPE: DNA
<213> ORGANISM: Rattus norvegicus

<400> SEQUENCE: 115
ccagaaagac tccagttgca gaacgaggga agaaggg                               37

<210> SEQ ID NO 116
<211> LENGTH: 23
<212> TYPE: DNA
<213> ORGANISM: Rattus norvegicus

<400> SEQUENCE: 116
agactccagt tgcagatcat gag                                              23

<210> SEQ ID NO 117
<211> LENGTH: 10
<212> TYPE: DNA
<213> ORGANISM: Rattus norvegicus

<400> SEQUENCE: 117
cgctgccgcc                                                             10

<210> SEQ ID NO 118
<211> LENGTH: 10
<212> TYPE: DNA
<213> ORGANISM: Rattus norvegicus

<400> SEQUENCE: 118
tacaacaggc                                                             10

<210> SEQ ID NO 119
<211> LENGTH: 23
<212> TYPE: DNA
<213> ORGANISM: Rattus norvegicus

<400> SEQUENCE: 119
agactccagt tgcagatcat gag                                              23

<210> SEQ ID NO 120
<211> LENGTH: 15
<212> TYPE: DNA
<213> ORGANISM: Rattus norvegicus

<400> SEQUENCE: 120
caatgacgag ggaag                                                       15
```

<210> SEQ ID NO 121
<211> LENGTH: 18
<212> TYPE: DNA
<213> ORGANISM: Rattus norvegicus

<400> SEQUENCE: 121
ccagaaagac tcccccct                                                   18

<210> SEQ ID NO 122
<211> LENGTH: 23
<212> TYPE: DNA
<213> ORGANISM: Rattus norvegicus

<400> SEQUENCE: 122
agactccagt tgcagatcat gag                                             23

<210> SEQ ID NO 123
<211> LENGTH: 15
<212> TYPE: DNA
<213> ORGANISM: Rattus norvegicus

<400> SEQUENCE: 123
cgctgacgag ggaag                                                      15

<210> SEQ ID NO 124
<211> LENGTH: 23
<212> TYPE: DNA
<213> ORGANISM: Rattus norvegicus

<400> SEQUENCE: 124
agactccagt tgcagatcat gag                                             23

<210> SEQ ID NO 125
<211> LENGTH: 15
<212> TYPE: DNA
<213> ORGANISM: Rattus norvegicus

<400> SEQUENCE: 125
tccgcacgag ggaag                                                      15

<210> SEQ ID NO 126
<211> LENGTH: 23
<212> TYPE: DNA
<213> ORGANISM: Rattus norvegicus

<400> SEQUENCE: 126
agactccagt tgcagatcat gag                                             23

<210> SEQ ID NO 127
<211> LENGTH: 15
<212> TYPE: DNA
<213> ORGANISM: Rattus norvegicus

<400> SEQUENCE: 127
aaataacgag ggaag                                                      15

<210> SEQ ID NO 128
<211> LENGTH: 28
<212> TYPE: DNA
<213> ORGANISM: Rattus norvegicus

<400> SEQUENCE: 128
tcagggttat tgtctgcaac tccagtct                                        28

<210> SEQ ID NO 129
<211> LENGTH: 23
<212> TYPE: DNA
<213> ORGANISM: Rattus norvegicus

<400> SEQUENCE: 129
agactggagt tgcagatcat gag                                          23

<210> SEQ ID NO 130
<211> LENGTH: 15
<212> TYPE: DNA
<213> ORGANISM: Rattus norvegicus

<400> SEQUENCE: 130
cgctgacgag ggaag                                                   15

<210> SEQ ID NO 131
<211> LENGTH: 29
<212> TYPE: DNA
<213> ORGANISM: Rattus norvegicus

<400> SEQUENCE: 131
tcagaaagac tggagttgca gatcatgag                                    29

<210> SEQ ID NO 132
<211> LENGTH: 20
<212> TYPE: DNA
<213> ORGANISM: Rattus norvegicus

<400> SEQUENCE: 132
cttcaacgag ggaagagggg                                              20

<210> SEQ ID NO 133
<211> LENGTH: 33
<212> TYPE: DNA
<213> ORGANISM: Rattus norvegicus

<400> SEQUENCE: 133
tcagaaagac tggagttgca gagggaagag ggg                               33

<210> SEQ ID NO 134
<211> LENGTH: 21
<212> TYPE: DNA
<213> ORGANISM: Rattus norvegicus

<400> SEQUENCE: 134
tcagaaagac tggaagaggg g                                            21

<210> SEQ ID NO 135
<211> LENGTH: 19
<212> TYPE: DNA
<213> ORGANISM: Rattus norvegicus

<400> SEQUENCE: 135
gttagagggg gaagagggg                                               19

<210> SEQ ID NO 136
<211> LENGTH: 24
<212> TYPE: DNA
<213> ORGANISM: Rattus norvegicus

<400> SEQUENCE: 136

```
acctaccgtc tcttcagggt ttta                                    24

<210> SEQ ID NO 137
<211> LENGTH: 31
<212> TYPE: DNA
<213> ORGANISM: Rattus norvegicus

<400> SEQUENCE: 137
acctaccgtc tcttcagggt aagtggtttt a                            31

<210> SEQ ID NO 138
<211> LENGTH: 27
<212> TYPE: DNA
<213> ORGANISM: Rattus norvegicus

<400> SEQUENCE: 138
acctaccgtc tcttcagggt ggtttta                                 27

<210> SEQ ID NO 139
<211> LENGTH: 24
<212> TYPE: DNA
<213> ORGANISM: Rattus norvegicus

<400> SEQUENCE: 139
acctaccgtc tcttcgtggt ttta                                    24

<210> SEQ ID NO 140
<211> LENGTH: 27
<212> TYPE: DNA
<213> ORGANISM: Rattus norvegicus

<400> SEQUENCE: 140
acctaccgtc tcttcagggt ggtttta                                 27

<210> SEQ ID NO 141
<211> LENGTH: 25
<212> TYPE: DNA
<213> ORGANISM: Rattus norvegicus

<400> SEQUENCE: 141
acctaccgtc tcttcagggt aagaa                                   25

<210> SEQ ID NO 142
<211> LENGTH: 27
<212> TYPE: DNA
<213> ORGANISM: Rattus norvegicus

<400> SEQUENCE: 142
acctaccgtc tcttcagggt ggtttta                                 27

<210> SEQ ID NO 143
<211> LENGTH: 24
<212> TYPE: DNA
<213> ORGANISM: Rattus norvegicus

<400> SEQUENCE: 143
acctaccgtc tcttcgtggt ttta                                    24

<210> SEQ ID NO 144
<211> LENGTH: 24
<212> TYPE: DNA
<213> ORGANISM: Rattus norvegicus

<400> SEQUENCE: 144
```
acctaccgtc tcttcgtggt ttta                                              24

<210> SEQ ID NO 145
<211> LENGTH: 24
<212> TYPE: DNA
<213> ORGANISM: Rattus norvegicus

<400> SEQUENCE: 145
acctaccgtc tcttcagggt ttta                                              24

<210> SEQ ID NO 146
<211> LENGTH: 27
<212> TYPE: DNA
<213> ORGANISM: Rattus norvegicus

<400> SEQUENCE: 146
acctaccgtc tcttcagggt ggtttta                                           27

<210> SEQ ID NO 147
<211> LENGTH: 24
<212> TYPE: DNA
<213> ORGANISM: Rattus norvegicus

<400> SEQUENCE: 147
acctaccgtc tcttcagggt ttta                                              24

<210> SEQ ID NO 148
<211> LENGTH: 35
<212> TYPE: DNA
<213> ORGANISM: Rattus norvegicus

<400> SEQUENCE: 148
acctaccgtc tcttcagggt aaaactgtgg tttta                                  35

<210> SEQ ID NO 149
<211> LENGTH: 25
<212> TYPE: DNA
<213> ORGANISM: Rattus norvegicus

<400> SEQUENCE: 149
acctaccgtc tcttctgtgg tttta                                             25

<210> SEQ ID NO 150
<211> LENGTH: 34
<212> TYPE: DNA
<213> ORGANISM: Rattus norvegicus

<400> SEQUENCE: 150
acctaccgtc tcttcagggt aasctgtggt ttta                                   34

<210> SEQ ID NO 151
<211> LENGTH: 25
<212> TYPE: DNA
<213> ORGANISM: Rattus norvegicus

<400> SEQUENCE: 151
acctaccgtc tcttctgtgg tttta                                             25

<210> SEQ ID NO 152
<211> LENGTH: 31
<212> TYPE: DNA
<213> ORGANISM: Rattus norvegicus

<400> SEQUENCE: 152
acctaccgtc tcttcagggt ctgtggtttt a                              31

<210> SEQ ID NO 153
<211> LENGTH: 24
<212> TYPE: DNA
<213> ORGANISM: Rattus norvegicus

<400> SEQUENCE: 153
acctaccgtc tcttcagggt ttta                                      24

<210> SEQ ID NO 154
<211> LENGTH: 25
<212> TYPE: DNA
<213> ORGANISM: Rattus norvegicus

<400> SEQUENCE: 154
acctaccgtc tcttcagtgg tttta                                     25

<210> SEQ ID NO 155
<211> LENGTH: 27
<212> TYPE: DNA
<213> ORGANISM: Rattus norvegicus

<400> SEQUENCE: 155
acctaccgtc tcttcagggt ggttta                                    27

<210> SEQ ID NO 156
<211> LENGTH: 32
<212> TYPE: DNA
<213> ORGANISM: Rattus norvegicus

<400> SEQUENCE: 156
acctaccgtc tcttcagggt tctgtggttt ta                             32

<210> SEQ ID NO 157
<211> LENGTH: 24
<212> TYPE: DNA
<213> ORGANISM: Rattus norvegicus

<400> SEQUENCE: 157
acctaccgtc tcttcagggt ttta                                      24

<210> SEQ ID NO 158
<211> LENGTH: 24
<212> TYPE: DNA
<213> ORGANISM: Rattus norvegicus

<400> SEQUENCE: 158
acctaccgtc tcttcagggt ttta                                      24

<210> SEQ ID NO 159
<211> LENGTH: 23
<212> TYPE: DNA
<213> ORGANISM: Rattus norvegicus

<400> SEQUENCE: 159
acctaccgtc tcttcaggtt tta                                       23

<210> SEQ ID NO 160
<211> LENGTH: 27
<212> TYPE: DNA
<213> ORGANISM: Rattus norvegicus

```
<400> SEQUENCE: 160
acctaccgtc tcttcagggt ggtttta                                          27

<210> SEQ ID NO 161
<211> LENGTH: 27
<212> TYPE: DNA
<213> ORGANISM: Rattus norvegicus

<400> SEQUENCE: 161
agacctaacc catcaatcct gggaagg                                          27

<210> SEQ ID NO 162
<211> LENGTH: 28
<212> TYPE: DNA
<213> ORGANISM: Rattus norvegicus

<400> SEQUENCE: 162
agacctaacc catcaaattc tgggaagg                                         28

<210> SEQ ID NO 163
<211> LENGTH: 29
<212> TYPE: DNA
<213> ORGANISM: Rattus norvegicus

<400> SEQUENCE: 163
agacctaacc catcaaattc ctgggaagg                                        29

<210> SEQ ID NO 164
<211> LENGTH: 25
<212> TYPE: DNA
<213> ORGANISM: Rattus norvegicus

<400> SEQUENCE: 164
agacctaacc catcaaattt gaagg                                            25

<210> SEQ ID NO 165
<211> LENGTH: 30
<212> TYPE: DNA
<213> ORGANISM: Rattus norvegicus

<400> SEQUENCE: 165
agacctaacc catcaaattc cctgggaagg                                       30

<210> SEQ ID NO 166
<211> LENGTH: 19
<212> TYPE: DNA
<213> ORGANISM: Rattus norvegicus

<400> SEQUENCE: 166
agacctaatc ctgggaagg                                                   19

<210> SEQ ID NO 167
<211> LENGTH: 32
<212> TYPE: DNA
<213> ORGANISM: Rattus norvegicus

<400> SEQUENCE: 167
agacctaacc catcaaattc ttcctgggaa gg                                    32

<210> SEQ ID NO 168
<211> LENGTH: 32
<212> TYPE: DNA
```

```
<213> ORGANISM: Rattus norvegicus

<400> SEQUENCE: 168
agacctaacc catcaaattc tatctgggaa gg                                      32

<210> SEQ ID NO 169
<211> LENGTH: 29
<212> TYPE: DNA
<213> ORGANISM: Rattus norvegicus

<400> SEQUENCE: 169
agacctaacc catcaaattc tatggaagg                                          29

<210> SEQ ID NO 170
<211> LENGTH: 26
<212> TYPE: DNA
<213> ORGANISM: Rattus norvegicus

<400> SEQUENCE: 170
agacctaacc catcaaattc tagagg                                             26

<210> SEQ ID NO 171
<211> LENGTH: 36
<212> TYPE: DNA
<213> ORGANISM: Rattus norvegicus

<400> SEQUENCE: 171
agacctaacc catcaaattc taawttcctg ggaagg                                  36

<210> SEQ ID NO 172
<211> LENGTH: 32
<212> TYPE: DNA
<213> ORGANISM: Rattus norvegicus

<400> SEQUENCE: 172
agacctaacc catcaaattc ttcctgggaa gg                                      32
```

US 10,362,771 B2

METHOD FOR KNOCK-IN OF DNA INTO TARGET REGION OF MAMMALIAN GENOME, AND CELL

CROSS-REFERENCE TO RELATED APPLICATIONS

This patent application is the U.S. national phase of International Patent Application No. PCT/JP2015/082279, filed on Nov. 17, 2015, which claims the benefit of Japanese Patent Application No. 2014-235898, filed Nov. 20, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 40,256 bytes ASCII (Text) file named "728782ReplacementSequenceListing.txt," created Jan. 9, 2019.

TECHNICAL FIELD

The present invention relates to a method for knock-in of a DNA into a target genomic region of a mammal, and cells.

BACKGROUND ART

In recent years, it has become possible to easily generate genetically modified animals via microinjection of artificial nucleases ZFNs/TALENs/CRISPRs into fertilized eggs in mammals, including mice and rats. Artificial nucleases introduce DNA double-strand breaks (DSBs) into target genes, and indel mutations are introduced via non-homologous end joining (NHEJ), which is a DSB repair mechanism, thereby generating knockout animals in which the target genes are disrupted. Since knockout animals can be generated more efficiently at lower cost in a shorter period of time than conventional gene modification techniques using ES cells, this technique has been widely used as a technique for generating genetically modified animals (NPL 1 and 2).

Attempts for knock-in have also been made to introduce a gene, such as GFP, into a target genomic region (or gene) using an artificial nuclease. A donor plasmid having an about 500 bp to 1 kbp sequence homologous to a target genomic region at each end of the knock-in sequence of GFP or the like is used. By introducing the donor plasmid into fertilized eggs together with an artificial nuclease, the artificial nuclease introduces DSB in the target sequence, and the gene, such as GFP, is knocked-in into the target sequence using the homologous sequences of the donor plasmid via homologous recombination (HR), which is another DSB repair mechanism (NPL 3 and 4).

In a method using no donor plasmid, a single base in a target gene can be substituted or a short DNA sequence of His-tag, LoxP, etc., which has a length of not greater than tens of bp, can be introduced, using single-stranded DNAs (ssODNs: single-stranded oligodeoxynucleotides). Knock-in animals can be generated easily and efficiently using single-strand annealing (SSA), which is a highly efficient DSB repair mechanism, by artificially synthesizing an ssODN comprising a 40- to 60-bp homologous sequence at each end of a base sequence to be introduced, and introducing the ssODN into fertilized eggs with an artificial nuclease (NPL 5 and 6).

When knock-in is performed using a donor plasmid, it is necessary to add, to a plasmid containing a gene to be knocked-in, sequences homologous to a target genomic region. Conventionally, such homologous sequences are amplified, for example, by PCR, ligated, and cloned in *Escherichia coli* to produce a donor plasmid, which takes time and effort. Moreover, it has been reported that HR is generally far less efficient than NHEJ in DSB repair for mammalian cells or fertilized eggs. Even when a donor plasmid is microinjected with an artificial nuclease, the efficiency of generating knock-in animals is notably lower than the efficiency of generating knockout animals (NPL 3 and 7).

When using ssODNs, knock-in is performed via DSB repair mechanism SSA using a single-stranded DNA, which is different from HR. It has thus been reported that the efficiency is higher than that when a donor plasmid is used (NPL 5 and 6). However, since only ssODNs of up to about 200 bp in length can be accurately synthesized, it is difficult to knock-in a long-chain gene sequence of GFP or the like (several hundred bp to several kilo bp).

CITATION LIST

Non-Patent Literature

NPL 1: Hsu P D et al., Cell, 2014
NPL 2: Mashimo T., Dev Growth Differ, 2014
NPL 3: Cui X et al., Nat Biotechnol, 2011
NPL 4: Yang H et al., Cell, 2013
NPL 5: Wang H et al., Cell, 2013
NPL 6: Yoshimi K et al., Nat Commun, 2014
NPL 7: Ponce de Leon V et al., PLoS One, 2014
NPL 8: Olsen P A et al., DNA Repair, 2009
NPL 9: Radecke S et al., Mol Ther, 2010

SUMMARY OF INVENTION

Technical Problem

An object of the present invention is to provide a technique for efficient knock-in of a DNA into the genome of a cell.

Solution to Problem

The present invention provides the following methods and cells.

Item 1. A method for knock-in of a donor DNA into the genome of a cell, comprising introducing at least one artificial nuclease system G capable of cleaving one or two target sequences G of the cell genome, the donor DNA, and two single-stranded oligonucleotides (ssODNs) into the cell, the artificial nuclease system G cleaving the one or two target sequences G on the cell genome to generate two DNA double-strand break (DSB) sites on the cell genome,
the two ssODNs being Up-ssODN complementary to DSB site g1, one of the DSB sites generated by the target sequence G cleavage of the cell genome, and to upstream introduction site D1 of the donor DNA, and Down-ssODN complementary to DSB site g2, the other DSB site of the cell genome, and to downstream introduction site D2 of the donor DNA, and
the donor DNA being knocked-in between the two DSB sites g1 and g2 in the one or two target sequences G of the cell genome using the two ssODNs (Up-ssODN and Down-ssODN).

Item 2. The method according to Item 1, wherein the donor DNA is a gene construct capable of being expressed in the cell.

Item 3. The method according to Item 1, wherein the donor DNA is a plasmid comprising one or two target sequences, the artificial nuclease system comprises artificial nuclease system G comprising Cas9 nuclease and one or two guide RNAs-G (gRNAs-G) corresponding to the one or two target sequences G of the cell genome, and artificial nuclease system D comprising Cas9 nuclease and one or two guide RNAs-D (gRNAs-D) corresponding to the one or two target sequences D of the donor DNA, the one or two target sequences G of the cell genome are cleaved by the artificial nuclease system G to generate DSB sites g1 and g2 on the cell genome, and the one or two target sequences D on the donor DNA plasmid are cleaved by the artificial nuclease system D to generate upstream introduction site D1 and downstream introduction site D2 of the plasmid-derived donor DNA to be knocked-in into the genome.

Item 4. The method according to Item 3, wherein one target sequence G is present on the cell genome, one target sequence D is present on the plasmid, the artificial nuclease system comprises artificial nuclease system G comprising Cas9 nuclease and guide RNA-G (gRNA-G) corresponding to the target sequence G, and artificial nuclease system D comprising Cas9 nuclease and guide RNA-D (gRNA-D) corresponding to the target sequence D, the gRNA-G comprises a strand complementary to the target sequence G, the gRNA-D comprises a strand complementary to the target sequence D, the target sequence G is cleaved by the artificial nuclease system G to generate DSB sites g1 and g2 on the cell genome, the target sequence D is cleaved by the artificial nuclease system D to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

Item 5. The method according to Item 3, wherein two target sequences G1 and G2 are present on the cell genome, one target sequence D is present on the plasmid, the artificial nuclease system comprises artificial nuclease system G1 comprising Cas9 nuclease and guide RNA-G1 (gRNA-G1) corresponding to the target sequence G1, artificial nuclease system G2 comprising Cas9 nuclease and guide RNA-G2 (gRNA-G2) corresponding to the target sequence G2, and artificial nuclease system D comprising Cas9 nuclease and guide RNA-D (gRNA-D) corresponding to the target sequence D, the gRNA-G1 and the gRNA-G2 respectively comprise individual strands complementary to the target sequences G1 and G2, the gRNA-D comprises a strand complementary to the target sequence D, the target sequences G1 and G2 are respectively cleaved by the artificial nuclease systems G1 and G2 to generate DSB sites g1 and g2 on the cell genome, the target sequence D is cleaved by the artificial nuclease system D to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

Item 6. The method according to Item 3, wherein one target sequence G is present on the cell genome, two target sequences D1 and D2 are present on the plasmid, the artificial nuclease system comprises artificial nuclease system G comprising Cas9 nuclease and guide RNA-G (gRNA-G) corresponding to the target sequence G, artificial nuclease system D1 comprising Cas9 nuclease and guide RNA-D1 (gRNA-D1) corresponding to the target sequence D1, and artificial nuclease system D2 comprising Cas9 nuclease and guide RNA-D2 (gRNA-D2) corresponding to the target sequence D2, the gRNA-G comprises a strand complementary to the target sequence G, the gRNA-D1 and the gRNA-D2 respectively comprise individual strands complementary to the target sequences D1 and D2, the target sequence G is cleaved by the artificial nuclease system G to generate DSB sites g1 and g2 on the cell genome, the target sequences D1 and D2 are respectively cleaved by the artificial nuclease systems D1 and D2 to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

Item 7. The method according to Item 3, wherein two target sequences G1 and G2 are present on the cell genome, two target sequences D1 and D2 are present on the plasmid, the artificial nuclease system comprises artificial nuclease system G1 comprising Cas9 nuclease and guide RNA-G1 (gRNA-G1) corresponding to the target sequence G1, artificial nuclease system G2 comprising Cas9 nuclease and guide RNA-G2 (gRNA-G2) corresponding to the target sequence G2, artificial nuclease system D1 comprising Cas9 nuclease and guide RNA-D1 (gRNA-D1) corresponding to the target sequence D1, and artificial nuclease system D2 comprising Cas9 nuclease and guide RNA-D2 (gRNA-D2) corresponding to the target sequence D2, the gRNA-G1 and the gRNA-G2 respectively comprise individual strands complementary to the target sequences G1 and G2, the gRNA-D1 and the gRNA-D2 respectively comprise individual strands complementary to the target sequences D1 and D2, the target sequences G1 and G2 are respectively cleaved by the artificial nuclease systems G1 and G2 to generate DSB sites g1 and g2 on the cell genome, the target sequences D1 and D2 are respectively cleaved by the artificial nuclease systems D1 and D2 to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

Item 8. The method according to any one of Items 1 to 7, wherein the cell is a fertilized egg.

Item 9. A cell comprising all or part of a plasmid introduced into its genome.

Item 10. The cell according to Item 9, wherein the plasmid is introduced into the genome at upstream and downstream DSB sites D1 and D2 generated by cleaving one or two target sequences D with Cas9.

Item 11. The cell according to Item 9 or 10, wherein the plasmid is introduced into the genome at a position between two DSB sites generated by cleaving one or two target sequences of the genome with Cas9.

Item 12. The cell according to any one of Items 9 to 11, wherein the cell is a fertilized egg.

Item 13. A non-human mammal into whose genome a plasmid is introduced, the non-human mammal comprising the cells according to any one of Items 9 to 12.

Item 14. The non-human mammal according to Item 13, which is humanized by knock-in of a plasmid comprising at least one gene derived from a human.

Advantageous Effects of Invention

The present invention makes it possible to generate knock-in animals several times to several tens of times more efficiently than conventional HR, by microinjecting artificial nuclease system(s), a donor DNA, such as a donor plasmid vector, that cannot undergo homologous recombination because of no or one sequence of not less than 18 consecutive bases homologous to a genome, and two ssODNs together into cells, in particular fertilized eggs, of a mammal, such as mice or rats. "Scissors (nuclease)" in the artificial nuclease system(s) induce DSB(s) in genomic target sequence(s) and further, as necessary, in the plasmid sequence, and the two ssODNs each having a sequence homologous to both the genome and the plasmid (Up-ssODN and Down-ssODN) act as "paste" to repair the DSB sites of the genome and the plasmid by joining them, thereby enabling accurate and efficient knock-in of the donor DNA on the specific genome. Since the DSB ends in the genome and donor DNA sequences were joined using DSB repair mechanism SSA, the method of the present invention is called "SSA-Mediated End Joining (SMEJ)." In addition, for example, a long gene sequence or a gene cluster can be replaced by cleaving two target sequences in a genome and one or two sites in a plasmid, i.e., a total of three or four sites.

The "SMEJ," which uses artificial nuclease system(s), a donor DNA, and two ssODNs together, makes it possible to knock-in a donor DNA of any length (in particular plasmid vector) targeted to the DNA sequence of, for example, any gene or promoter on a mammalian genome. The advantages of the present invention are as follows: 1) since knock-in animals can be generated at a high efficiency of 10 to 30% of animals born by microinjection, a reduction in experimental animals, shortened experiment time, and higher efficiency can be expected; 2) when a plasmid is used as a donor DNA, any existing plasmid can be used as is without adding, to the plasmid, homologous sequences, thus eliminating the need for complicated operations for preparing a plasmid; 3) When an artificial nuclease CRISPR is used, it only takes several days to a week for preparation of Cas9 nuclease and gRNAs, and several days for synthesis of ssODNs, and injection can thus be carried out within a short period of time from experimental design; 4) the present invention enables knock-in using a long bacterial artificial chromosome (BAC) plasmid of 200 kb or more, which has been difficult to knock-in by conventional gene modification techniques using ES cells etc., and enables replacement of a gene cluster region; 5) the present invention can be used not only for mice and rats, but also for any experimental animals whose fertilized eggs can be used (such as rabbits, pigs, sheep, cows, and monkeys).

The present invention is described herein as a method for knock-in of a donor DNA into one site on a genome; however, with the present invention, two or more knock-ins can be performed simultaneously by introducing, into cells, guide RNAs involved in two or more knock-ins together with Cas9 nuclease and two or more donor DNAs.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3 illustrates CAG-GFP knock-in in the rat Rosa26 locus using the 2H2O method.

FIG. 6 illustrates the DNA sequence of the rat Rosa26 gene: target sequence of gRNA (blue; CGTGATCTG-CAACTGGAGTC) and PAM sequence (green; CCT); upstream ssODN (underlined in yellow; CCCTGGGCCTG-GAAGATTCCCTTCCCCCTTCTTC) and downstream ssODN (underlined in red; GATCTGCAACTG-GAGTCTTTCTGGAAGATAGGCGGGAGTC); primers used for PCR analysis (surrounded by boxes); and site cleaved by CRISPR (red ▼).

FIG. 7 illustrates the DNA sequence of the pCAG-GFP plasmid: target sequence of gRNA (blue; CAGGGTTATT-GTCTCATGAG) and PAM sequence (green; CGG); upstream ssODN (underlined in yellow; GAGCGGATA-CATATTTGAATGTATTTAGAAAAATAAACAA) and downstream ssODN (underlined in red; TTCAATATTATT-GAAGCATTTATCAGGGTTATTGTCTCAT); primers used for PCR analysis (surrounded by six individual boxes); and site cleaved by CRISPR (red ▼).

FIG. 8 illustrates sequence analysis of the rat Rosa26 gene in 17 rat pups obtained by microinjection. Various knockout and knock-in mutations were observed (CRISPR-mediated KO/KI mutations at rat Rosa26 loci).

FIG. 10 illustrates the DNA sequence of the mouse Rosa26 gene: target sequence of gRNA (blue; CGTGATCT-GCAACTCCAGTC) and PAM sequence (green; CCT); upstream ssODN (underlined in yellow; GCCCTGGGC-CTGGGAGAATCCCTTCCCCCTCTTCCCTCGT) and downstream ssODN (underlined in red; GATCTG-CAACTCCAGTCTTTCTAGAAGATGGGCGGGAGTC); primers used for PCR analysis (surrounded by four individual boxes); and site cleaved by CRISPR (red ▼).

FIG. 12 illustrates sequence analysis of the mouse Rosa26 gene in six mouse pups obtained by microinjection. Various knockout and knock-in mutations were observed (CRISPR-mediated KO/KI mutations at mouse Rosa26 loci).

FIG. 13(a) is a diagram illustrating gene replacement by the SMEJ method. Three gRNAs cleave the upstream and downstream of the rat Cyp2d gene cluster, and a human CYP2D6 gene (CAG) plasmid (top), and two ssODNs (ssODN-1 and ssODN-2) induce joining of the DSB cleavage ends (bottom). FIG. 13(b) illustrates PCR analysis of 23 rat pups. FIG. 13(c) illustrates sequence analysis of a rat in which the rat Cyp2d gene cluster was replaced by human CYP2D6 (#18) and a rat Cyp2d cluster deletion rat (#2).

FIG. 14 illustrates the DNA sequence of the rat Cyp2d gene cluster: target sequences of gRNA (blue; CCGTCTCT-TCAGGGTAACTG) and PAM sequences (green; TGG); ssODN sequences (underlined in blue; CTAGTGACA-GGGCCTGGTGCCCAGGAGTCAGGCAAACACCTAC-CGTCTCTTCAGGGTAA); primers used for PCR analysis (surrounded by eight individual boxes); and sites cleaved by CRISPR (red ▼).

FIG. 15 illustrates sequence analysis of the upstream and downstream of the rat Cyp2d gene cluster in 23 rat pups obtained by microinjection. Various knockout and knock-in mutations were observed.

DESCRIPTION OF EMBODIMENTS

Figure 1:
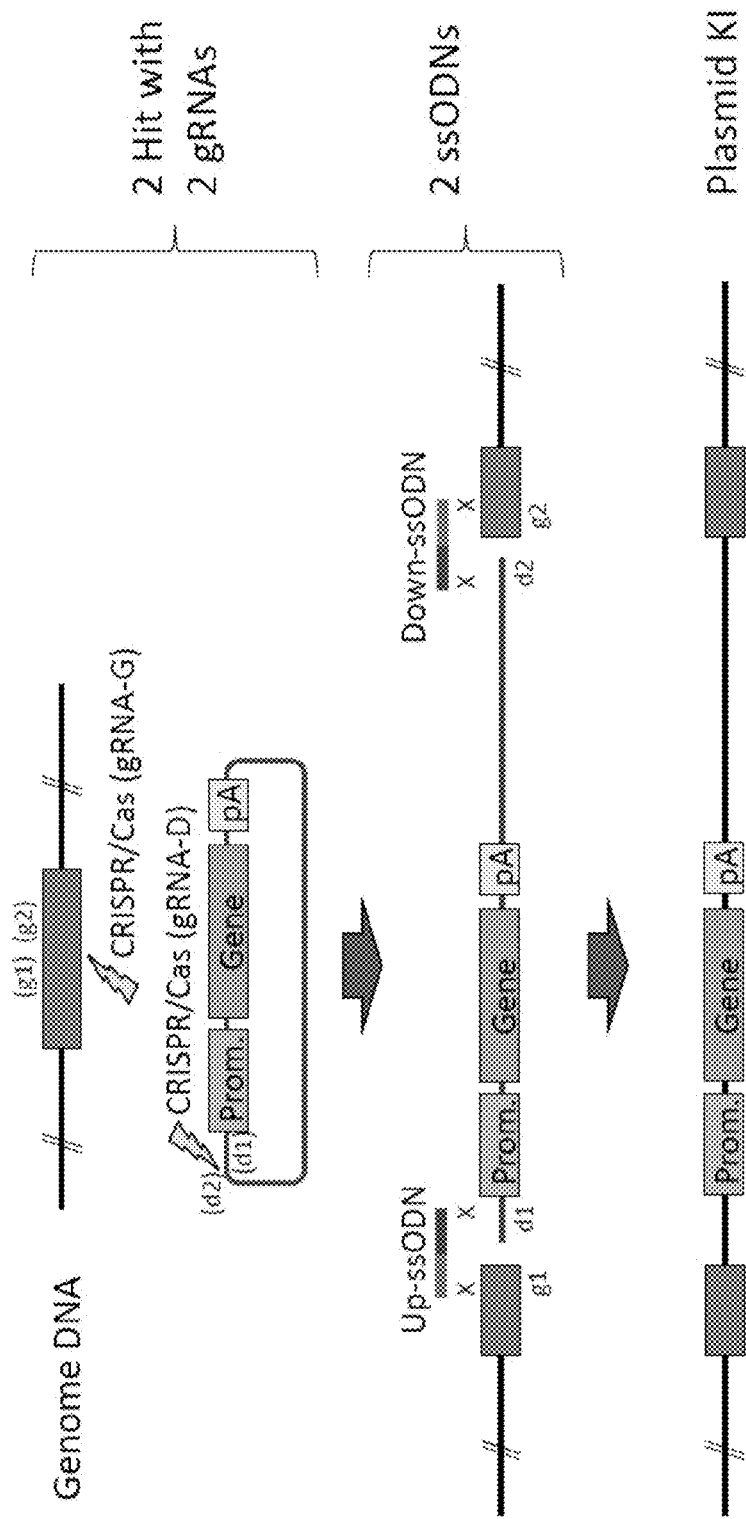
FIG. 1 illustrates a two-hit two-oligo (2H2O) method: vector knock-in via ssODNs-mediated end joining.

In the figures, the following abbreviations are used:
(g1): potential g1 that becomes upstream DSB site g1 generated when target sequence G or G1 is cleaved by artificial nuclease system G or G1;
(g2): potential g2 that becomes downstream DSB site g2 generated when target sequence G or G2 is cleaved by artificial nuclease system G or G2;
(d1): potential d1 that becomes upstream DSB site d1 generated when target sequence D or D1 is cleaved by artificial nuclease system D or D1;
(d2): potential d2 that becomes downstream DSB site d2 generated when target sequence D or D2 is cleaved by artificial nuclease system D or D2;
Up-ssODN: single-stranded oligonucleotide complementary to both the upstream DSB site g1 of the genome and the upstream DSB site d1 of the donor DNA; and
Down-ssODN: single-stranded oligonucleotide complementary to both the downstream DSB site g2 of the genome and the downstream DSB site d2 of the donor DNA.

The genome editing technology used in the present invention is, for example, a technology using ZFNs, TALENs, or CRISPR/Cas, and preferably CRISPR/Cas.

The term "zinc finger nuclease" (ZFN) as used herein refers to an artificial nuclease comprising a nucleic acid cleavage domain conjugated to a binding domain that comprises a zinc finger array. In an embodiment, the cleavage domain is the cleavage domain of the type II restriction enzyme FokI. Zinc finger nucleases can be designed to cleave any target sequence in a given genome for cleavage.

The term "transcription activator-like effector nuclease" (TALEN) as used herein refers to an artificial nuclease comprising a transcription activator-like (TAL) effector DNA binding domain in addition to a DNA cleavage domain, for example, a FokI domain. Modular assembly schemes for generating engineered TALE constructs have been reported (e.g., Zhang, Feng et al. (2011) Nature Biotechnology 29 (2); this document is incorporated herein by reference).

Clustered Regularly Interspaced Short Palindromic Repeats (CRISPR)/CRISPR-associated (Cas) use a nuclease (RGN; RNA-guided nuclease) and a guide RNA (gRNA). Examples of nucleases (RGNs) include type I, II, and III nucleases. The nuclease is preferably a type II nuclease, and particularly preferably Cas9. Although the nuclease used for CRISPR may be described as "Cas9 nuclease" hereinafter, nucleases other than Cas9 may be used.

The gRNA comprises a chimera in which crRNA (CRISPR RNA), which has a strand complementary to a target sequence adjacent to a PAM in a genome or a donor DNA (including a plasmid), and trans-activating crRNA (tracrRNA) are linked by a suitable connecting sequence.

In the case of CRISPR/Cas, a preferable artificial nuclease system comprises Cas9 nuclease and a guide RNA, and induces DSB cleavage of a target sequence.

Artificial nuclease system G is used when there is one target sequence in a genome. The artificial nuclease system G comprises Cas9 nuclease and guide RNA-G, and induces DSB cleavage of a target sequence G to generate DSB sites g1 and g2. The guide RNA-G comprises a strand complementary to the target sequence G adjacent to a PAM.

Artificial nuclease system G1 and artificial nuclease system G2 are used when there are two target sequences in a genome. The artificial nuclease system G1 comprises Cas9 nuclease and guide RNA-G1, and induces DSB cleavage of target sequence G1 to generate upstream DSB site g1. The artificial nuclease system G2 comprises Cas9 nuclease and guide RNA-G2, and induces DSB cleavage of target sequence G2 to generate downstream DSB site g2. The guide RNA-G1 comprises a strand complementary to the target sequence G1 adjacent to a PAM, and the guide RNA-G 2 comprises a strand complementary to the target sequence G2 adjacent to a PAM.

Figure 2A:
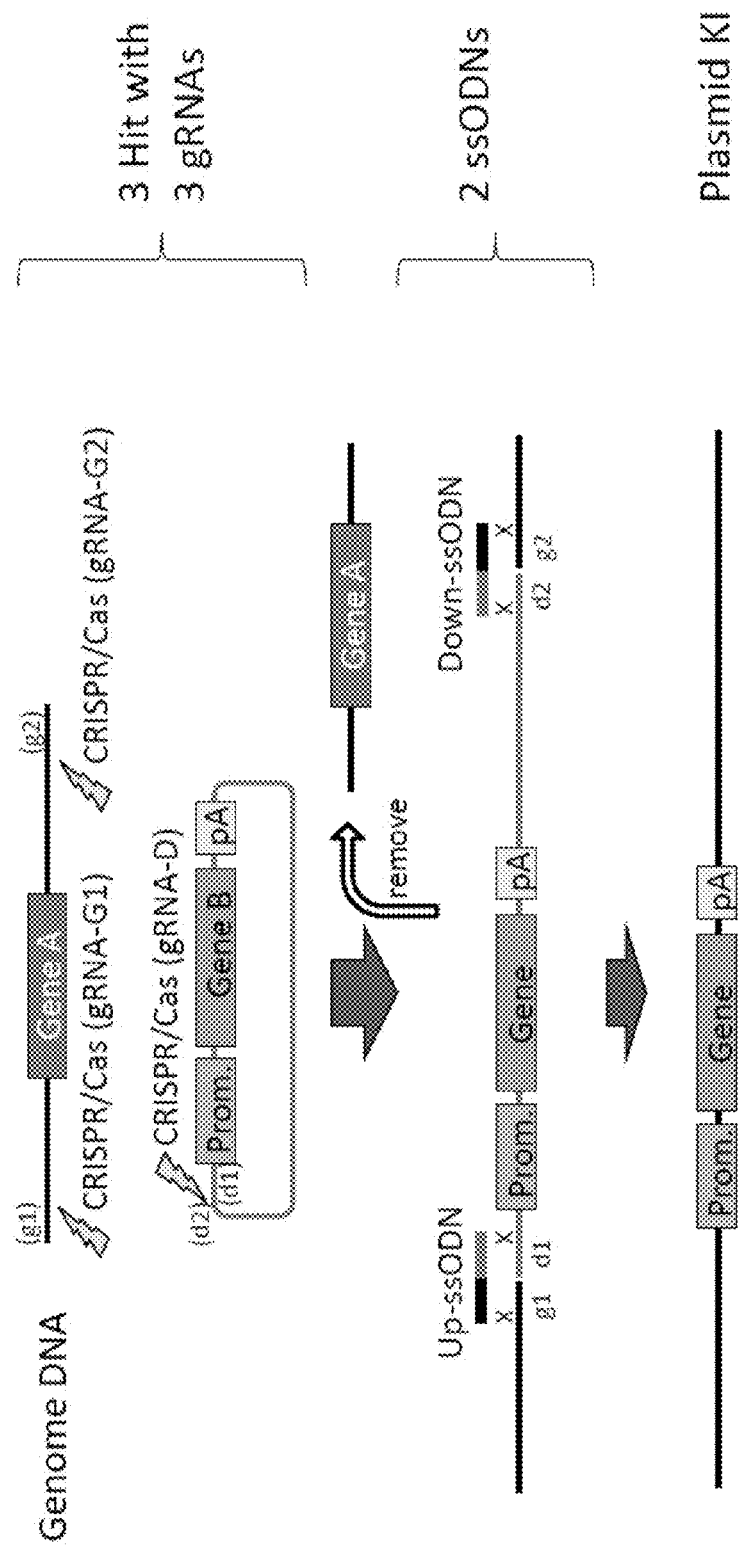
FIG. 2A illustrates a three-hit two-oligo (3H2O) method for gene replacement.
Figure 2B:
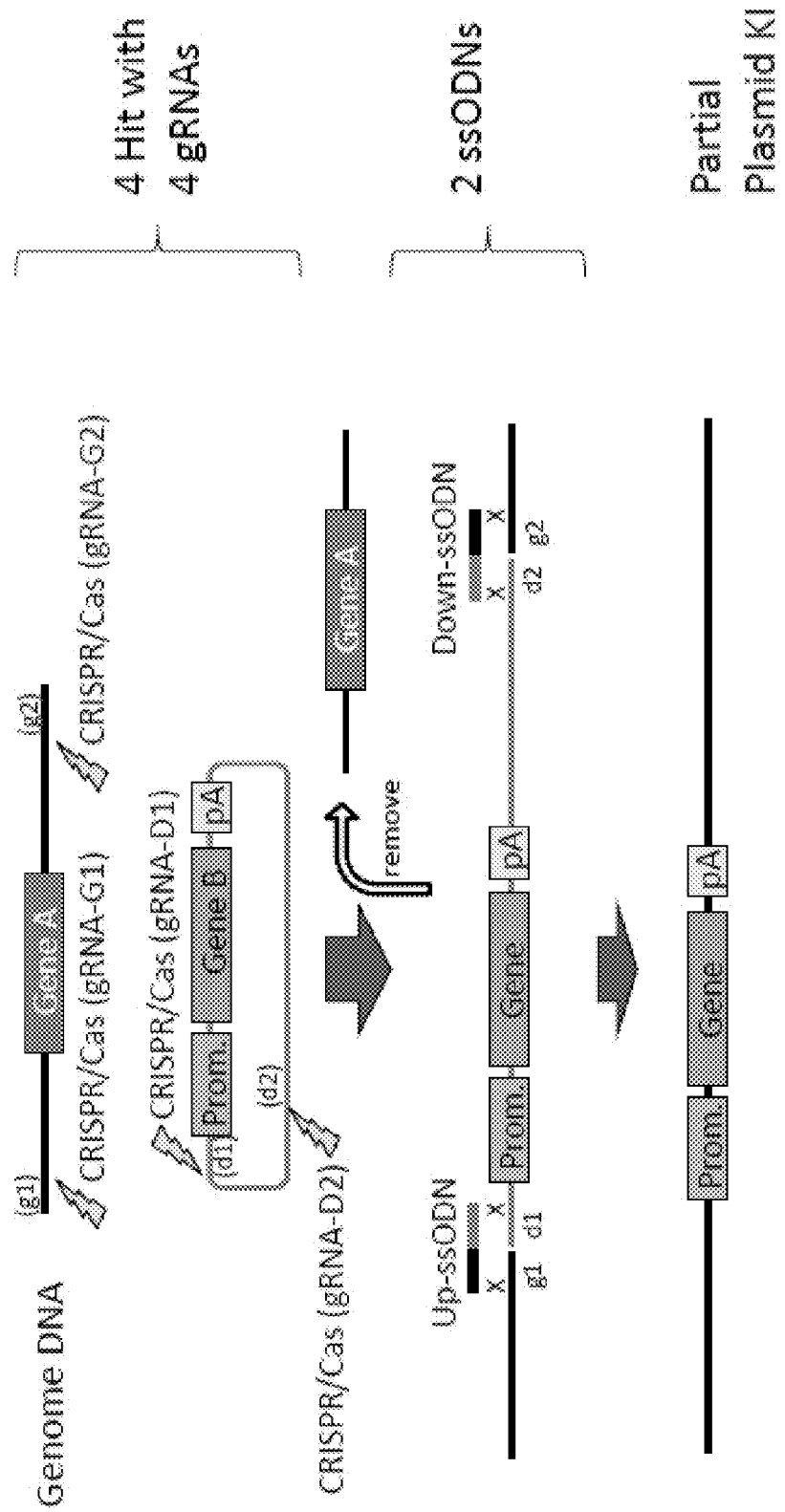
FIG. 2B illustrates a four-hit two-oligo (4H2O) method for gene replacement.

Artificial nuclease system D induces DSB cleavage of target sequence D of a donor DNA, and preferably comprises Cas9 nuclease and guide RNA-D. The guide RNA-D comprises a strand complementary to the target sequence D adjacent to a PAM. FIGS. 2A, 2B, and 3 show the cases when the donor DNA is a plasmid. When the donor DNA is a circular DNA like a plasmid, upstream introduction site d1 and downstream introduction site d2 are simultaneously generated by DSB cleavage of one target sequence D. When the donor DNA is a linear DNA, either upstream introduction site d1 or downstream introduction site d2 is generated by DSB cleavage of one target sequence D. When the donor DNA is a plasmid having two target sequences D1 and D2, one of the two portions into which the plasmid is divided is knocked-in as a donor DNA into a cell genome.

Examples of artificial nuclease systems include (i) a combination of the artificial nuclease system G and the artificial nuclease system D (2H2O, FIG. 1), (ii) a combination of the artificial nuclease system G1, the artificial nuclease system G2, and the artificial nuclease system D (3H2O, FIG. 2A), (iii) a combination of the artificial nuclease system G, the artificial nuclease system D1, and the artificial nuclease system D2 (3H2O), and (iv) a combination of the artificial nuclease system G1, the artificial nuclease system G2, the artificial nuclease system D1, and the artificial nuclease system D2 (4H2O, FIG. 2B).

The constituents of artificial nuclease systems are Cas9 nuclease, the guide RNA-G, and the guide RNA-D in the case of (i); Cas9 nuclease, the guide RNA-G1, the guide RNA-G2, and the guide RNA-D in the case of (ii); Cas9 nuclease, the guide RNA-G, the guide RNA-D1, and the guide RNA-D2 in the case of (iii); and Cas9 nuclease, the guide RNA-G1, the guide RNA-G2, the guide RNA-D1, and the guide RNA-D2 in the case of (iv). Cas9 nuclease and the guide RNAs can be introduced into cells using, for example, plasmids or virus vectors expressing these.

The length of target sequence on the cell genome is not particularly limited. When using CRISPR/Cas, the target sequence is composed of 17 to 27 bases, preferably 18 to 25 bases, more preferably 19 to 22 bases, even more preferably 19 to 20 bases, and particularly preferably 20 bases. When using the CRISPR/Cas system, the target sequence (sense strand or antisense strand) on the cell genome is adjacent to a PAM (proto-spacer adaptor motif) sequence, and the target sequence on the cell genome can be determined by the position adjacent to the PAM sequence. The PAM sequence is not particularly limited and is, for example, NGG (N is any base).

Figure 4:
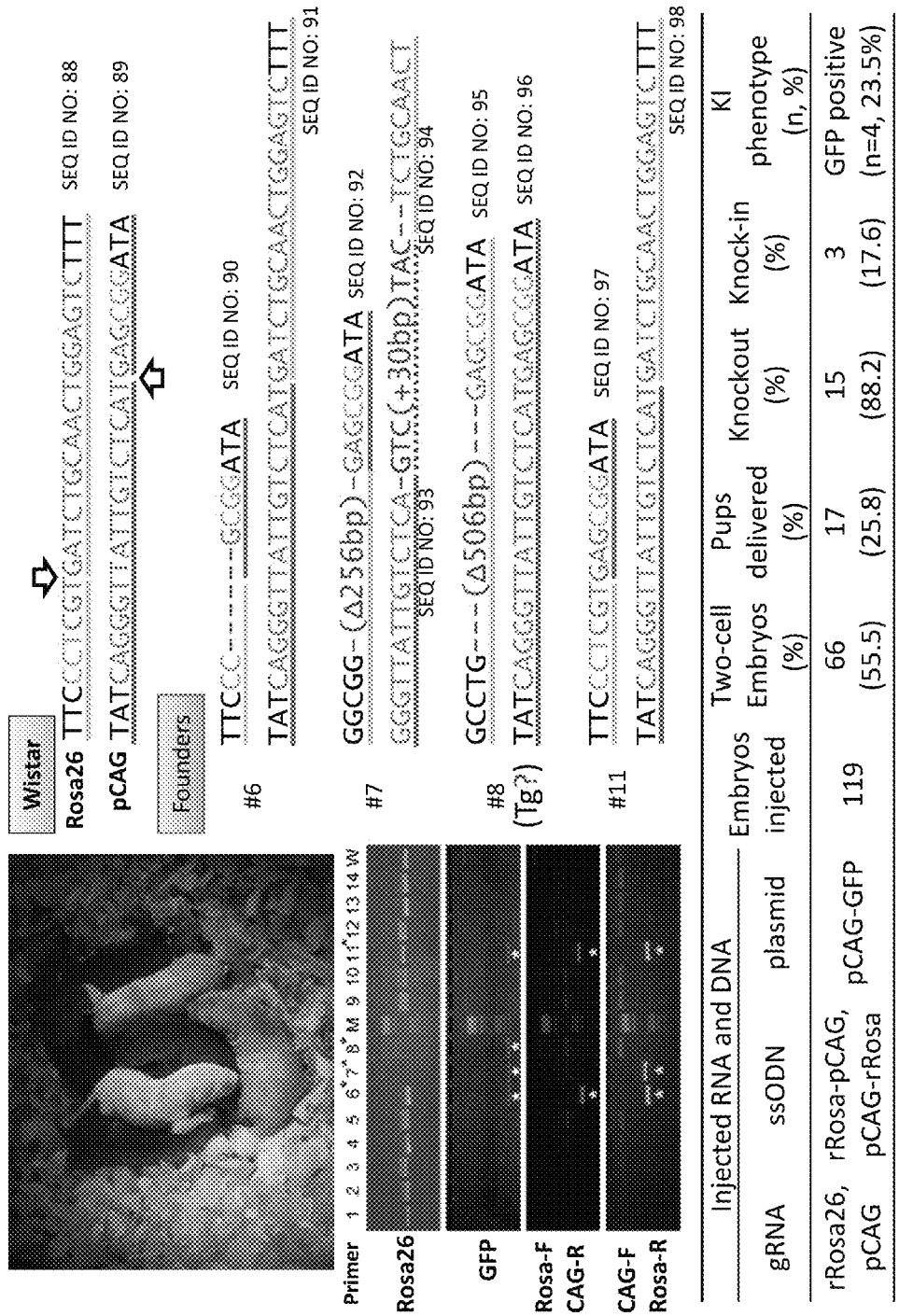
FIG. 4 illustrates generation of GFP knock-in rats with CRISPR/Cas9.

The number of target sequences on the genome may be one or two. For example, when two target sequences on the genome are cleaved, a predetermined sequence can be excised, and a donor DNA is inserted into the target genomic region, from which the predetermined sequence has been excised, thereby replacing a portion of the genomic DNA. Replacement in the genomic DNA can be performed by the three-hit two-oligo method (FIG. 2A). Insertion of a donor DNA into a target sequence on the genome can be performed by the two-hit two-oligo method (FIG. 1). FIG. 3 shows a method for knock-in of CAG-GFP into the rat Rosa26 locus using the 2H2O method, and the results. FIG. 4 shows a method for obtaining GFP knock-in rats using CRISPR/Cas9, and the results.

As the donor DNA of the present invention, any DNA can be used, and the donor DNA is preferably a gene construct capable of being expressed in cells, such as a plasmid. The donor DNA is introduced into a target site in linear form. Thus, when a circular plasmid is used as the donor DNA, the plasmid is cleaved in a cell to produce a linear plasmid, after which the linear plasmid is introduced as a donor DNA between the DSB sites in the genome generated by cleavage using the artificial nuclease system(s). The artificial nuclease system D can be used for cleavage of the target sequence D on a plasmid. Specifically, the target sequence D is determined by placing it adjacent to a PAM sequence of the plasmid, and target sequence(s) (target sequence G when the genome contains one target sequence as in the case of 2H2O; target sequences G1 and G2 when the genome contains two target sequences as in the case of 3H2O) are determined by placing the target sequence(s) adjacent to one or two PAM sequences in the genome, thereby enabling the target sequences of both the genome and the plasmid to be cleaved by the artificial nuclease systems. The target sequence(s) on the genome and the target sequence of the plasmid may be the same or different. When the one or two target sequences of the genome differ from the target sequence of the plasmid, artificial nuclease systems that enable cleavage of two or three target sequences (e.g., a combination of the artificial nuclease system G and the artificial nuclease system D; and a combination of the artificial nuclease system G1, the artificial nuclease system G2, and the artificial nuclease system D) can be used. Unlike homologous recombination, the knock-in in the present invention does not require homology arms in the donor DNA. In the present invention, DSB cleavage site(s) (e.g., "▼" (two sites) in FIG. 5d, and "▼" in FIGS. 6 and 7) are introduced within the target sequence(s). When the two set of DSB ends, each set consisting of one genome and one donor DNA, are joined with ssODNs, they may be ligated without introducing mutation (e.g., #11 of FIG. 5d), or mutation may be introduced (e.g., #6, 7, and 8 of FIG. 5d).

The length of donor DNA is not particularly limited, and may be generally 10 bp or more, 20 bp or more, 40 bp or more, 80 bp or more, 200 bp or more, 400 bp or more, 800 bp or more, 1 kbp or more, 2 kbp or more, 3 kbp or more, 4 kbp or more, 8 kbp or more, 10 kbp or more, 20 kbp or more, 40 kbp or more, 80 kbp or more, 100 kbp or more, or 200 kbp or more. An advantage of the method of the present invention is that even a donor DNA having a very long length of 200 kbp or more can be introduced efficiently. The donor DNA may be of a different origin than the host. For example, a donor DNA derived from a human can be knocked-in into the genome of a mammal other than humans.

The donor DNA may be one gene, or a gene cluster region may be knocked-in as the donor DNA.

Each of the ssODNs used in the present invention has a sequence complementary to one of the DSB ends generated by cleavage in the genome, and to one of the ends of the donor DNA. Use of the two ssODNs as "paste" enables the donor DNA to be joined to the sites generated by cleavage in the genome, thereby significantly increasing knock-in efficiency. The length of each ssODN sequence complementary to the respective end is 10 to 100 bases, preferably 12 to 80 bases, more preferably 15 to 60 bases, and even more preferably 20 to 40 bases; and the total length of each ssODN having a sequence complementary to the two respective ends is 20 to 200 bases, preferably 24 to 160 bases, more preferably 30 to 120 bases, and even more preferably 40 to 80 bases.

The term "knock-in" as used herein encompasses both insertion of a donor DNA into a genome, and replacement by a donor DNA in a genome.

The cells used in the present invention may be any cells. Examples include somatic cells, ES cells, iPS cells and like pluripotent stem cells, fertilized eggs, and the like. Fertilized eggs are preferable because genetically modified mammals in which a donor DNA is knocked-in can easily be obtained. For example, mammals in which all drug-metabolizing enzymes are humanized, human disease animal models in which at least one gene involved in human disease is introduced, mammalian models in which all genes related to a specific organ or tissue are humanized, and the like can easily be obtained by the method of the present invention.

In the present invention, two ssODNs (Up-ssODN and Down-ssODN) are used. The Up-ssODN comprises a sequence complementary to both the upstream (5' side) d1 of the sense strand encoding the gene of the donor DNA and DSB site g1, which is one of the DSB sites of the genome. The Down-ssODN comprises a sequence complementary to both the downstream (3' side) d2 of the sense strand encoding the gene of the donor DNA and DSB site g2, which is the other DSB site of the genome (FIGS. 1 to 3).

Each respective DSB site of the genome and the upstream or downstream introduction site of the donor DNA may be directly ligated, or mutation such as insertion or deletion may occur between the sites. In any case, the gene in the donor DNA can function.

By microinjection into fertilized eggs, these ssODNs act in the nucleus, enabling increased knock-in efficiency. Whether the microinjection in fertilized eggs is performed in the cytoplasm or the nucleus, the donor DNA can be efficiently knocked-in.

Examples of mammals include humans, mice, rats, rabbits, goats, dogs, cats, cows, pigs, monkeys, and the like.

Further, the present invention relates to cells in which a plasmid is introduced into their genome, or cells in which a long DNA (gene construct) of 300 bp or more, 500 bp or more, 1 kbp or more, 2 kbp or more, 3 kbp or more, 5 kbp or more, 10 kbp or more, 20 kbp or more, 30 kbp or more, 50 kbp or more, 100 kbp or more, or 200 kbp or more is inserted. There have heretofore been no cells in which a plasmid or a long donor DNA is introduced. Thus, the present invention provides novel cells.

A particularly preferred embodiment of the present invention is a non-human mammal obtained by knock-in of a donor DNA into fertilized eggs. Attempts have been made to introduce a human gene into a non-human mammal for humanization; however, conventional methods are limited due to difficulty in introducing a large DNA. With the present invention, even a long sequence of 200 kbp or more can efficiently be introduced; therefore, a gene cluster of a non-human mammal can easily be modified to the corresponding human gene cluster, and the majority of DNA can be humanized by repeating knock-in of a donor DNA.

Insertion of a plasmid or a long donor DNA may be confirmed by sequencing or by detecting the expression product protein by, for example, Western blotting.

In the present invention, since the artificial nuclease systems introduce double-strand breaks (DSBs) into the target genome and donor DNA sequences as "scissors," and the two ssODNs join and repair the genome and the donor DNA as "paste," the donor DNA can be knocked-in on the specific genome accurately and efficiently. A long gene sequence, a gene cluster, or the like can be replaced, by cleaving two target sequences in the genome and cleaving one or two sites in the plasmid.

In the present invention, simply by preparing the artificial nuclease system(s) and ssODNs, any existing plasmid can be knocked-in as is, targeting the DNA sequence of any gene, promoter, or the like on the genome of mammals. Further, the present invention enables not only knockout but also efficient knock-in in mammals other than mice, for which there have heretofore been no ES cells.

EXAMPLES

Examples are given below to illustrate the present invention in more detail; however, the present invention is not limited to these Examples.

Example 1

(1) Experimental Method

In this experiment, Cas9 expression plasmid (hCas9: Addgene ID#41815) and gRNA expression plasmid (pDR274: Addgene ID#42250) obtained from Addgene (www.addgene.org/CRISPR) were used. Modifications such as introduction of a T7 promoter upstream of the Cas9 gene were made in the Cas9 expression plasmid. pCAG plasmid was obtained from Riken BioResource Center, and the GFP gene and the human CYP2D6 gene were introduced.

Target sequences were determined using CRISPR Design Tool (crispr.genome-engineering.org), and gRNA expression plasmids that recognize the sequences were prepared (Table 1). Using the Cas9 expression plasmid, in vitro transcription, poly A addition reaction, and RNA purification were sequentially performed, thereby preparing Cas9 mRNA. gRNAs were also prepared by performing in vitro transcription and RNA purification. Further, ssODNs each having a sequence homologous to one of the sites generated by cleavage in a genome and to one of the sites generated by cleavage in a plasmid were designed and obtained (Table 2). Female sexually mature rats of the Wistar:Jcl strain were superovulated, and fertilized eggs were obtained by natural mating. Mouse fertilized eggs were obtained using female mice of the C57BL/6JJcl strain. A mixed solution of Cas9 mRNA in an amount of 100 µg/ml, gRNAs each in an amount of 50 µg/ml, ssODNs each in an amount of 50 µg/ml, and plasmid in an amount of 5 µg/ml was prepared using RNase free water and microinjected into the male pronuclei of the fertilized eggs. The fertilized eggs in which the solution was microinjected were cultured at 37° C. under 5% $CO_2$ overnight, and then transferred into the oviduct of pseudopregnant female rats or mice. About 3 weeks after transfer, the rats or mice delivered pups.

From the obtained pups, GFP-positive pups were selected using a light for checking GFP fluorescence. In addition, tissues were collected from the pups, DNA was extracted, and PCR, electrophoresis, and sequence analysis were performed using the primers shown in Table 3 to confirm introduction of the plasmid into the genomic target sequence. The details of this experimental method are described in a reference (Nat Commun., 2014, June 26; 5: 4240). This document is incorporated herein by reference.

(2) Experimental Results

Figure 5:
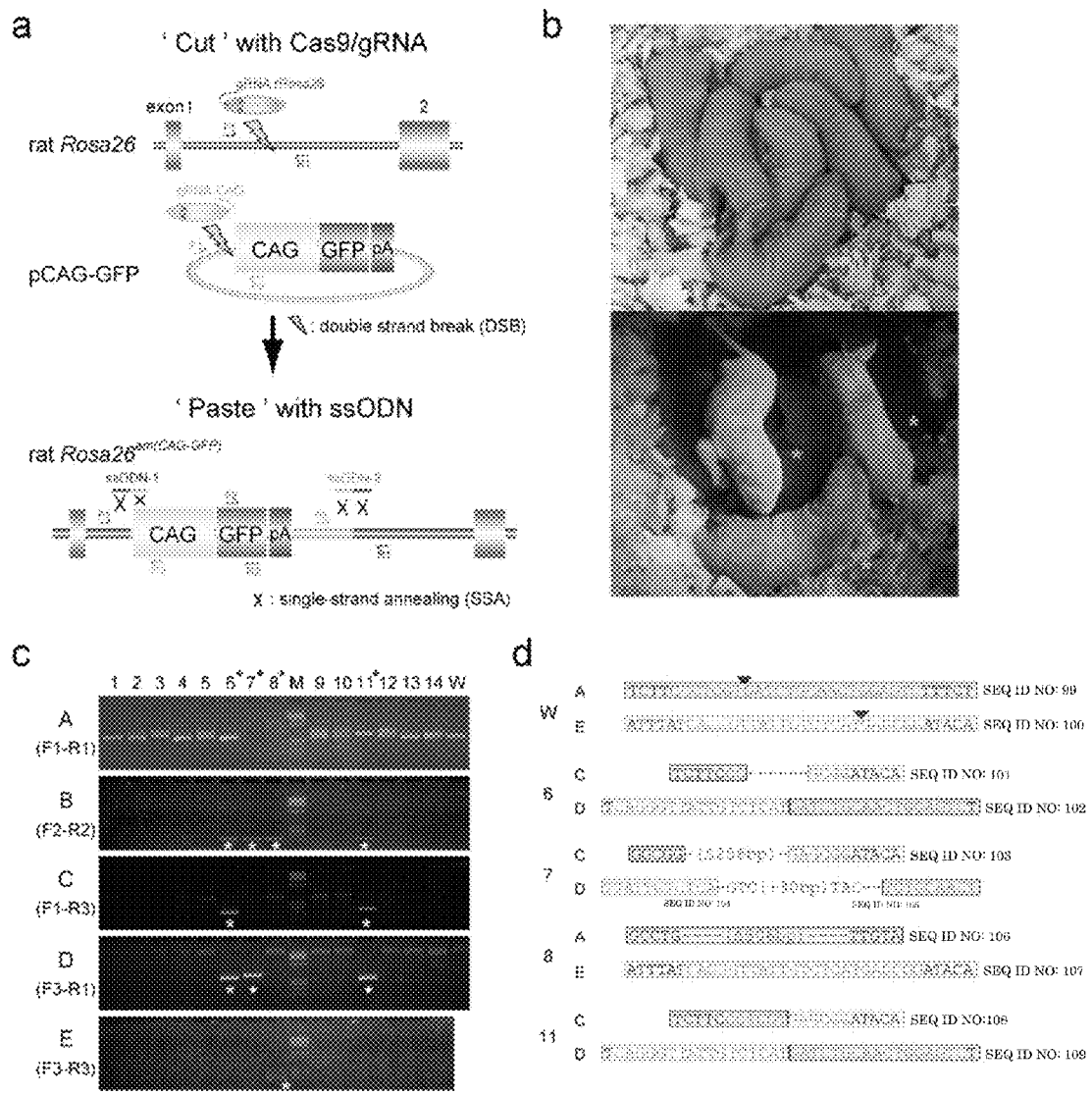
FIG. 5(a) is a diagram illustrating knock-in using the SMEJ method. Two gRNAs cleave intron 1 of the rat Rosa26 gene and a pCAG-GFP plasmid (top), and two ssODNs (ssODN-1 and ssODN-2) induce joining of DSB cleavage ends (bottom).
FIG. 5(b) illustrates rats into which GFP was introduced.
FIG. 5(c) illustrates PCR analysis of 14 rat pups.
FIG. 5(d) illustrates sequence analysis of GFP-positive rats (#6, 7, 8, and 11).
Figure 9:
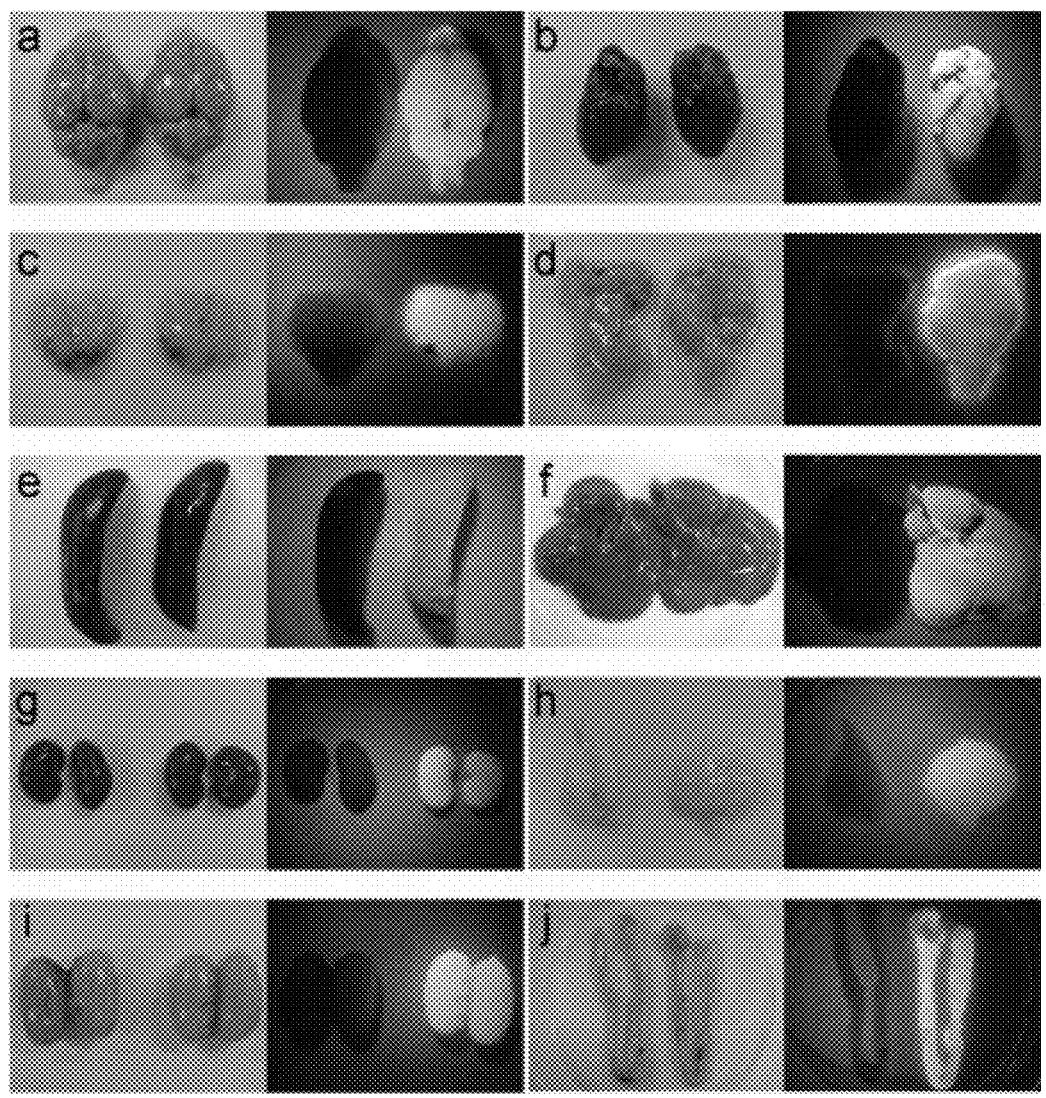
FIG. 9 illustrates GFP expression in each organ of a GFP knock-in rat (#11: right) and a control rat (left). a: brain, b: heart, c: thymus, d: pancreas, e: spleen, f: liver, g: kidneys, h: fat, i: testes, j: large intestine.

This experiment was performed for cleaving a target sequence in the rat Rosa26 gene and a target sequence in pCAG-GFP plasmid at the same time using CRISPR/Cas9, which acts as "scissors," and accurately and efficiently knocking-in the pCAG-GFP into the rat Rosa26 using two ssODNs, which act as "paste" (FIG. 5a). A target sequence was designed between the first exon and the second exon of the rat Rosa26 gene, and designed upstream of the CAG promoter of the pCAG-GFP, and gRNAs were prepared (Table 1, and FIGS. 6 and 7). In addition, ssODNs were designed for joining the upstream of the Rosa26 cleavage site and the downstream of the pCAG plasmid cleavage site, and the downstream of the Rosa26 cleavage site and the upstream of the pCAG-GFP cleavage site (Table 2). These were introduced into fertilized eggs together with the pCAG-GFP. Of the obtained 17 pups, 4 pups expressed GFP in the entire body (Table 4 and FIG. 5b). PCR analysis showed amplification of the GFP-specific sequence in rat Nos. 6, 7, 8, and 11 (FIG. 5c). To confirm whether the pCAG-GFP was integrated into the Rosa26 region, investigation was performed using a combination of primers for the rat Rosa26 and for the pCAG-GFP; as a result, amplification was observed in rat Nos. 6, 7, and 11, confirming that the pCAG-GFP was integrated into the Rosa26 region (FIG. 5c). In rat No. 8, it was confirmed that the cleavage site of the pCAG-GFP was present on the genome. The results of sequence analysis confirmed that, in rat No. 11, the pCAG-GFP was introduced in the sequences at both the upstream and downstream as designed in the ssODNs (FIG. 5d); in rat No. 6, deletion of six bases was observed in the upstream; and in rat No. 7, insertion and deletion of multiple bases were observed at both the upstream and downstream ends. Not only these knock-in mutations were observed, but also knockout mutations were confirmed in 15 pups (FIG. 8). The plasmid knock-in mutation obtained in rat No. 11 was stably transmitted to the offspring. In addition, no mutations were observed in the off-target sequences. The results of pathological analysis confirmed that, in this knock-in line, GFP was stably expressed in organs in the entire body (FIG. 9).

Figure 11:
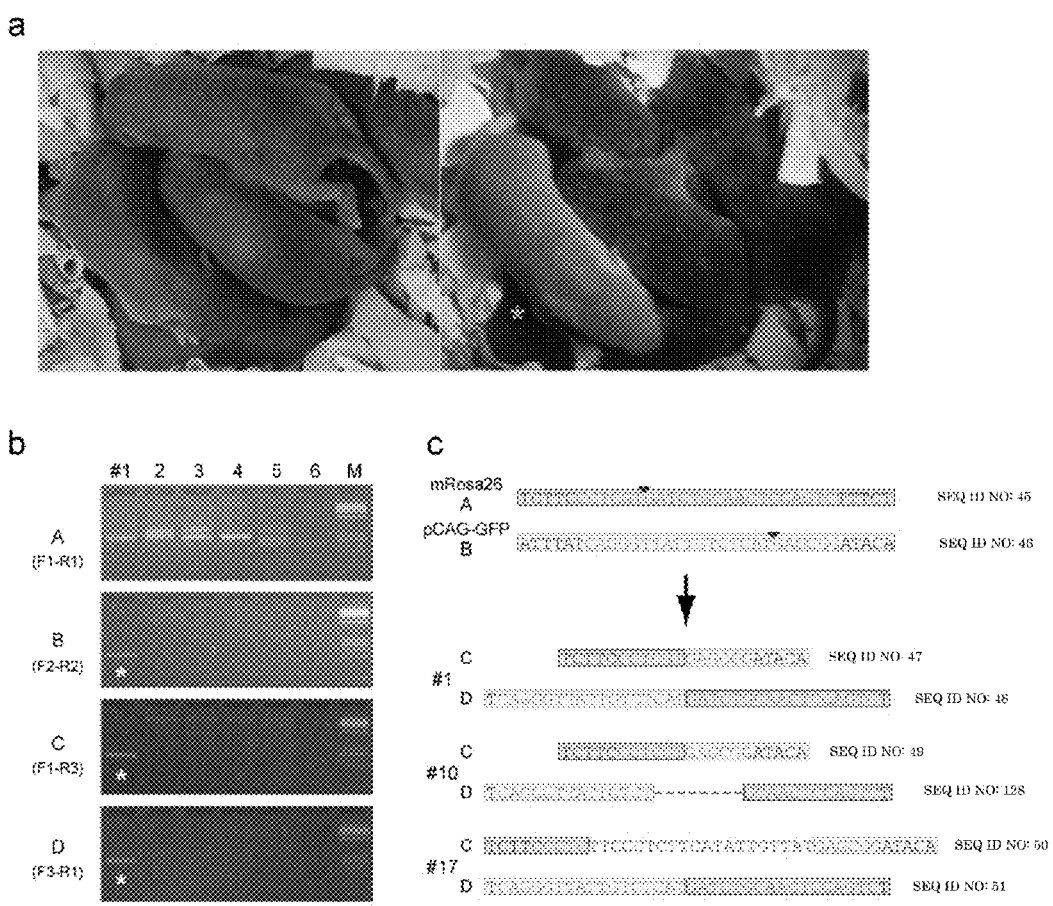
FIG. 11(a) illustrates mice in which a pCAG-GFP plasmid was introduced into the mouse Rosa26 gene by the SMEJ method.
FIG. 11(b) illustrates PCR analysis of six mouse pups.
FIG. 11(c) illustrates sequence analysis of GFP-positive mice (#1, 10, and 17).

In the same manner as in the case of rats, a target sequence was designed between the first exon and the second exon of the mouse Rosa26 gene, and gRNAs and ssODNs were prepared (FIG. 10 and Tables 1 and 2). The mouse-Rosa26-target-site-specific gRNA and the ssODNs were introduced together with pCAG-GFP. Of the obtained 31 pups (Table 4), 3 pups expressed GFP in the entire body (FIG. 11a). PCR analysis showed amplification of the GFP-specific sequence in mouse Nos. 1, 10, and 17. Investigation using a combination of primers for the mouse Rosa26 and for the pCAG-GFP confirmed that the pCAG-GFP was integrated into the Rosa26 region in the three mice (FIG. 11b). It was confirmed that in mouse No. 1, the pCAG-GFP was introduced in the sequences at both the upstream and downstream of the pCAG-GFP as designed in the ssODNs (FIG. 11c). In mouse No. 10, deletion of eight bases was observed at the downstream. In mouse No. 17, insertion of 18 bases was observed at the upstream. In addition, knockout mutations were confirmed in all of the obtained pups (FIG. 12).

Finally, for CYP2D6 gene, one of the cytochrome P450 (CYP) enzymes, which are central enzymes involved in drug metabolism, the rat Cyp2d gene cluster (Cyp2d1-5) was replaced by the human CYP2D6 gene (FIG. 13a). A target sequence was designed at each of a total of three sites, i.e., two sequences, one in each of the upstream and the downstream of the rat Cyp2d gene cluster, and one sequence in the upstream of a pCAG plasmid containing CYP2D6 gene (pCYP2D6), and gRNAs were prepared (FIG. 14, Table 1). In addition, ssODNs for joining the upstream of the Cyp2d cluster cleavage site and the downstream of the plasmid cleavage site, and the downstream of the Cyp2d cluster cleavage site and the upstream of the plasmid cleavage site were designed (Table 2). These were introduced into fertilized eggs together with pCYP2D6 (Table 4). PCR analysis showed amplification of the CYP2D6-specific sequence in rat Nos. 1, 3, 8, and 18 (FIG. 13b). To confirm whether the CYP2D6 was integrated into the Cyp2d cluster region, investigation was performed using a combination of primers for the rat Cyp2d and for the pCYP2D6; as a result, amplification was observed in rat No. 18. Further, the results of sequence analysis confirmed that, in rat No. 18, the pCYP2D6 was introduced in the sequences at both the upstream and downstream as designed in the ssODNs (FIG. 13c). In rat No. 2, PCR amplification by the upstream and downstream primers of the Cyp2d was observed, and large deletion in the rat Cyp2d gene cluster was confirmed. At the same time, many mutations were also confirmed in the target sequences of the Cyp2d gene (FIG. 15).

TABLE 1

Table 1. DNA sequence used for gRNA synthesis

| gRNA name | Forward | Reverse |
|---|---|---|
| rRosa26 | TAGGGACTCCAGTTGCAGATCACG | AAACCGTGATCTGCAACTGGAGTC |
| mRosa26 | TAGGGACTGGAGTTGCAGATCACG | AAACCGTGATCTGCAACTCCAGTC |
| pCAGGS | TAGGCAGGGTTATTGTCTCATGAG | AAACCTCATGAGACAATAACCCTG |
| rCyp2d up | TAGGCCGTCTCTTCAGGGTAACTG | AAACCAGTTACCCTGAAGAGACGG |
| rCyp2d down | TAGGTAACCCATCAAATTCTATCC | AAACGGATAGAATTTGATGGGTTA |

TABLE 2

Table 2. DNA sequence of single-stranded DNA (ssODN)

| | |
|---|---|
| rRosa26-CAGGS | CCCTGGGCCTGGAAGATTCCCTTCCCCCTTCTTCCCTCGTGAGC GGATACATATTTGAATGTATTTAGAAAAATAAACAA |
| CAGGS-rRosa26 | TTCAATATTATTGAAGCATTTATCAGGGTTATTGTCTCATGATC TGCAACTGGAGTCTTTCTGGAAGATAGGCGGGAGTC |
| mRosa26-CAGGS | GCCCTGGGCCTGGGAGAATCCCTTCCCCCTCTTCCCTCGTGAGC GGATACATATTTGAATGTATTTAGAAAAATAAACAA |
| CAGGS-mRosa26 | TTCAATATTATTGAAGCATTTATCAGGGTTATTGTCTCATGATC TGCAACTCCAGTCTTTCTAGAAGATGGGCGGGAGTC |
| rCyp2dUp-CAGGS | CTAGTGACAGGGCCTGGTGCCCAGGAGTCAGGCAAAACACCTAC CGTCTCTTCAGGGTAAGAGCGGATACATATTTGAATGTATTTAG AAAAATAAACAAATAGGGGTTCCGCGCACATT |
| CAGGS-rCyp2dDown | AATACTCATACTCTTCCTTTTTCAATATTATTGAAGCATTTATC AGGGTTATTGTCTCATTCCTGGGAAGGTCTCTTGAAGCACTCAT CTTGGCTTCTTGGCTTCTGTAGTTCTCCTAGC |

TABLE 3

Table 3. Primer sequence used for gene mutation analysis

| Primer name | Forward | Reverse | PCR size (bp) |
|---|---|---|---|
| rRosa26 | AAGGGAGCTGCAGTGGAGTA | CCCAGGTGAGTGCCTAGTCT | 360 |
| mRosa26 | AAGGGAGCTGCAGTGGAGTA | CCGAAAATCTGTGGGAAGTC | 297 |

TABLE 3-continued

Table 3. Primer sequence used for gene mutation analysis

| Primer name | Forward | Reverse | PCR size (bp) |
| --- | --- | --- | --- |
| GFP | CTACCCCGACCACATGAAG | CTTGTGCCCCAGGATGTT | 202 |
| pCAGGS | ACTTTCACCAGCGTTTCTGG | AATCAATGTCGACCCAGGTG | 237 |
| rCyp2d up | GGTCACCTCCTCTCCATGTG | GCTAGGAGTCCAGGTGCTTG | 274 |
| rCyp2d down | CCATTTGGGCCATAAAACTT | GCTGGCTGGTGACTACACTG | 253 |
| hCYP2D6 | TGGCATGAAGGACTGGATTT | AAGGCCTTTCCTTCTGGTGT | 153 |

TABLE 4

Efficiency of genome editing by SMEJ method

| Species | Injected gRNA and DNA | | | Embryos injected | Two-cell embryos (%) | Pups delivered (%) | Knockout (%) | Knock-in (%) | KI phenotype (n, %) |
| --- | --- | --- | --- | --- | --- | --- | --- | --- | --- |
| | gRNA | ssODN | Plasmid | | | | | | |
| rat | Rosa26, CAGGS | Rosa-CAG, pCAG-Rosa | pCAG-GFP | 119 | 66 (55.5) | 17 (25.8) | 15 (88.2) | 3 (17.6) | GFP-positive 4 (23.5%) |
| mouse | mRosa26, CAGGS | mRosa-CAG, CAG-mRosa | pCAG-GFP | 165 | 132 (80.0) | 31 (23.5) | 31 (100) | 3 (9.7) | GFP-positive 3 (9.7%) |
| rat | rCyp2d-up, rCyp2d-down, CAGGS | rCyp2dUp-CAGGS, CAGGS-rCyp2dDown: | pCYP2D6 | 130 | 72 (55.4) | 23 (31.9) | rCyp2dUp: 22 (95.7) rCyp2dDown 21 (91.3) rCyp2d-Del: 1 (4.3) | 1 (4.3) | hCYP2D6-positive 4 (17.4%) |

INDUSTRIAL APPLICABILITY

The present invention enables not only knockout using artificial nucleases ZFNs/TALENs/CRISPRs, but also knock-in using various donor plasmids; i.e., the present invention enables "free genome editing." With the present invention, a reporter gene such as the gene encoding GFP fluorescent protein can be introduced into a stable expression staining region, such as Rosa26 locus, or a reporter gene can be bound to the N-terminus or the C-terminus of a target gene. This greatly advances commissioned business for knock-in animal generation in genetically modified animals.

In addition, the present invention makes it possible to efficiently generate a "genome humanized animal" in which a gene of a mammal is disrupted and a human gene is introduced. With the present invention, animal models such as disease animal models having genes involved in various human diseases or humanized animal models having, for example, a gene involved in the origin of the human race, can be generated. Genetically modified animal models newly developed in such a manner are widely used not only for experimental animals, but also, for example, for drug discovery and regenerative medicine research.

With this technique, GFP knock-in mice and rats, and genome humanized animals in which a rat homologous gene is replaced by a human gene, have already been successfully generated very efficiently. This technique is thus expected to be widely used as a practical technique in the future.

The invention claimed is:

1. A method for knock-in of a donor DNA into the genome of a cell, comprising introducing at least one artificial nuclease system G capable of cleaving one or two target sequences G of the cell genome, the donor DNA, and two single-stranded oligonucleotides (ssODNs) into the cell, the artificial nuclease system G cleaving the one or two target sequences G on the cell genome to generate two DNA double-strand break (DSB) sites on the cell genome, the two ssODNs being Up-ssODN complementary to DSB site g1, one of the DSB sites generated by the target sequence G cleavage of the cell genome, and to upstream introduction site D1 of the donor DNA, and Down-ssODN complementary to DSB site g2, the other DSB site of the cell genome, and to downstream introduction site D2 of the donor DNA, and the donor DNA being knocked-in between the two DSB sites g1 and g2 in the one or two target sequences G of the cell genome using the two ssODNs (Up-ssODN and Down-ssODN), wherein the donor DNA is a plasmid comprising one or two target sequences, the artificial nuclease system comprises artificial nuclease system G comprising Cas9 nuclease and one or two guide RNAs-G (gRNAs-G) corresponding to the one or two target sequences G of the cell genome, and artificial nuclease system D comprising Cas9 nuclease and one or two guide RNAs-D (gRNAs-D) corresponding to the one or two target sequences D of the donor DNA, the one or two target sequences G of the cell genome are cleaved by the artificial nuclease system G to generate DSB sites g1 and g2 on the cell genome, and the one or two target sequences D on the donor DNA plasmid are cleaved by the artificial nuclease system D to generate upstream introduction site D1 and downstream introduction site D2 of the plasmid-derived donor DNA to be knocked-in into the genome.

2. The method according to claim 1, wherein the donor DNA is a gene construct capable of being expressed in the cell.

3. The method according to claim 1, wherein one target sequence G is present on the cell genome, one target sequence D is present on the plasmid, the artificial nuclease system comprises artificial nuclease system G comprising Cas9 nuclease and guide RNA-G (gRNA-G) corresponding to the target sequence G, and artificial nuclease system D comprising Cas9 nuclease and guide RNA-D (gRNA-D) corresponding to the target sequence D, the gRNA-G comprises a strand complementary to the target sequence G, the gRNA-D comprises a strand complementary to the target sequence D, the target sequence G is cleaved by the artificial nuclease system G to generate DSB sites g1 and g2 on the cell genome, the target sequence D is cleaved by the artificial nuclease system D to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

4. The method according to claim 1, wherein two target sequences G1 and G2 are present on the cell genome, one target sequence D is present on the plasmid, the artificial nuclease system comprises artificial nuclease system G1 comprising Cas9 nuclease and guide RNA-G1 (gRNA-G1) corresponding to the target sequence G1, artificial nuclease system G2 comprising Cas9 nuclease and guide RNA-G2 (gRNA-G2) corresponding to the target sequence G2, and artificial nuclease system D comprising Cas9 nuclease and guide RNA-D (gRNA-D) corresponding to the target sequence D, the gRNA-G1 and the gRNA-G2 respectively comprise individual strands complementary to the target sequences G1 and G2, the gRNA-D comprises a strand complementary to the target sequence D, the target sequences G1 and G2 are respectively cleaved by the artificial nuclease systems G1 and G2 to generate DSB sites g1 and g2 on the cell genome, the target sequence D is cleaved by the artificial nuclease system D to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

5. The method according to claim 1, wherein one target sequence G is present on the cell genome, two target sequences D1 and D2 are present on the plasmid, the artificial nuclease system comprises artificial nuclease system G comprising Cas9 nuclease and guide RNA-G (gRNA-G) corresponding to the target sequence G, artificial nuclease system D1 comprising Cas9 nuclease and guide RNA-D1 (gRNA-D1) corresponding to the target sequence D1, and artificial nuclease system D2 comprising Cas9 nuclease and guide RNA-D2 (gRNA-D2) corresponding to the target sequence D2, the gRNA-G comprises a strand complementary to the target sequence G, the gRNA-D1 and the gRNA-D2 respectively comprise individual strands complementary to the target sequences D1 and D2, the target sequence G is cleaved by the artificial nuclease system G to generate DSB sites g1 and g2 on the cell genome, the target sequences D1 and D2 are respectively cleaved by the artificial nuclease systems D1 and D2 to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

6. The method according to claim 1, wherein two target sequences G1 and G2 are present on the cell genome, two target sequences D1 and D2 are present on the plasmid, the artificial nuclease system comprises artificial nuclease system G1 comprising Cas9 nuclease and guide RNA-G1 (gRNA-G1) corresponding to the target sequence G1, artificial nuclease system G2 comprising Cas9 nuclease and guide RNA-G2 (gRNA-G2) corresponding to the target sequence G2, artificial nuclease system D1 comprising Cas9 nuclease and guide RNA-D1 (gRNA-D1) corresponding to the target sequence D1, and artificial nuclease system D2 comprising Cas9 nuclease and guide RNA-D2 (gRNA-D2) corresponding to the target sequence D2, the gRNA-G1 and the gRNA-G2 respectively comprise individual strands complementary to the target sequences G1 and G2, the gRNA-D1 and the gRNA-D2 respectively comprise individual strands complementary to the target sequences D1 and D2, the target sequences G1 and G2 are respectively cleaved by the artificial nuclease systems G1 and G2 to generate DSB sites g1 and g2 on the cell genome, the target sequences D1 and D2 are respectively cleaved by the artificial nuclease systems D1 and D2 to generate upstream introduction site D1 and downstream introduction site D2 of the plasmid-derived donor DNA, the DSB site g1, which is one of the DSB sites, and the upstream DSB site D1 are joined using the upstream single-stranded oligonucleotide (Up-ssODN), and the DSB site g2, which is the other DSB site, and the downstream DSB site D2 are joined using the downstream single-stranded oligonucleotide (Down-ssODN).

7. The method according to claim 1, wherein the cell is a fertilized egg.

* * * * *